US010624709B2

(12) United States Patent
Remm

(10) Patent No.: US 10,624,709 B2
(45) Date of Patent: Apr. 21, 2020

(54) ROBOTIC SURGICAL TOOL WITH MANUAL RELEASE LEVER

(71) Applicant: Ethicon LLC, Guaynabo, PR (US)

(72) Inventor: Thomas Remm, Milford, OH (US)

(73) Assignee: Ethicon LLC, Guaynabo, PR (US)

( * ) Notice: Subject to any disclaimer, the term of this patent is extended or adjusted under 35 U.S.C. 154(b) by 328 days.

(21) Appl. No.: 15/794,490

(22) Filed: Oct. 26, 2017

(65) Prior Publication Data
US 2019/0125464 A1    May 2, 2019

(51) Int. Cl.
*A61B 34/00*    (2016.01)
*A61B 17/29*    (2006.01)
(Continued)

(52) U.S. Cl.
CPC .............. *A61B 34/71* (2016.02); *A61B 17/29* (2013.01); *A61B 18/1445* (2013.01); *A61B 34/37* (2016.02); *A61B 90/08* (2016.02); *A61B 17/062* (2013.01); *A61B 17/068* (2013.01); *A61B 17/1285* (2013.01); *A61B 17/3201* (2013.01); *A61B 18/1482* (2013.01); *A61B 2017/00225* (2013.01); *A61B 2017/00407* (2013.01);
(Continued)

(58) Field of Classification Search
CPC ......... A61B 34/71; A61B 34/37; A61B 90/08; A61B 17/29; A61B 18/1445; A61B 34/35; A61B 2034/305; A61B 17/062; A61B 17/068; A61B 17/1285; A61B 17/3201; A61B 18/1482; A61B 2017/00407; A61B 2017/00477; A61B 2017/0046; A61B 2017/2932; A61B 34/30

See application file for complete search history.

(56) References Cited

U.S. PATENT DOCUMENTS 8,831,782 B2    9/2014    Itkowitz
2006/0161138 A1*  7/2006    Orban, III .............. A61B 46/10
                                                  606/1
(Continued)

FOREIGN PATENT DOCUMENTS

WO    2014151621 A1    9/2014
WO    2014151952 A1    9/2014
WO    2017044406 A1    3/2017

OTHER PUBLICATIONS

ISRWO of corresponding PCT/US2018/056401 dated Jan. 29, 2019.

*Primary Examiner* — Katrina M Stransky
(74) *Attorney, Agent, or Firm* — Vorys, Sater, Seymour and Pease LLP

(57) ABSTRACT

A surgical tool includes a drive housing that houses drive cable capstans operatively coupled to corresponding drive inputs, an elongate shaft that extends from the drive housing, and an end effector operatively coupled to a distal end of the elongate shaft. A plurality of drive cables extend between the drive housing and the end effector, and each drive cable is associated with a corresponding one of drive cable capstans. A manual release assembly is coupled to the drive housing and includes a release lever that is manually movable between a stowed position, where the drive cable capstans are operatively coupled to the drive inputs, to an actuated position, where the drive cable capstans are disengaged from the plurality of drive inputs. Moving the release lever to the actuated position also rotates the drive cable capstans to manually articulate the end effector.

19 Claims, 11 Drawing Sheets

(51) Int. Cl.
  *A61B 34/37*   (2016.01)
  *A61B 17/00*   (2006.01)
  *A61B 34/30*   (2016.01)
  *A61B 18/14*   (2006.01)
  *A61B 90/00*   (2016.01)
  *A61B 17/062*  (2006.01)
  *A61B 17/068*  (2006.01)
  *A61B 17/128*  (2006.01)
  *A61B 17/3201* (2006.01)
  *A61B 18/00*   (2006.01)

(52) U.S. Cl.
  CPC ............ *A61B 2017/00477* (2013.01); *A61B 2017/00725* (2013.01); *A61B 2017/2932* (2013.01); *A61B 2018/00595* (2013.01); *A61B 2034/305* (2016.02)

(56) References Cited

U.S. PATENT DOCUMENTS

| | | | |
|---|---|---|---|
| 2007/0119274 A1* | 5/2007 | Devengenzo | B25J 15/04 74/490.01 |
| 2008/0046122 A1* | 2/2008 | Manzo | A61B 1/00149 700/245 |
| 2008/0119870 A1* | 5/2008 | Williams | A61B 34/71 606/130 |
| 2008/0140088 A1* | 6/2008 | Orban, III | A61B 34/30 606/130 |
| 2008/0308604 A1* | 12/2008 | Timm | A61B 17/07207 227/175.1 |
| 2009/0088774 A1* | 4/2009 | Swarup | A61B 34/37 606/130 |
| 2010/0011900 A1* | 1/2010 | Burbank | A61B 34/71 74/490.06 |
| 2010/0011901 A1* | 1/2010 | Burbank | A61B 34/71 74/490.06 |
| 2010/0016852 A1* | 1/2010 | Manzo | A61B 34/71 606/46 |
| 2010/0016853 A1* | 1/2010 | Burbank | A61B 34/71 606/48 |
| 2010/0069833 A1* | 3/2010 | Wenderow | A61M 25/0113 604/95.01 |
| 2010/0082041 A1* | 4/2010 | Prisco | B25J 9/1045 606/130 |
| 2011/0071543 A1* | 3/2011 | Prisco | A61B 17/0218 606/130 |
| 2011/0288573 A1* | 11/2011 | Yates | A61B 17/07207 606/170 |
| 2011/0290855 A1* | 12/2011 | Moore | A61B 17/072 227/180.1 |
| 2011/0295270 A1* | 12/2011 | Giordano | A61B 17/105 606/130 |
| 2012/0150154 A1* | 6/2012 | Brisson | A61B 17/00 606/1 |
| 2012/0298719 A1* | 11/2012 | Shelton, IV | A61B 17/07207 227/176.1 |
| 2014/0000411 A1* | 1/2014 | Shelton, IV | A61B 34/30 74/650 |
| 2014/0001234 A1* | 1/2014 | Shelton, IV | A61B 17/07207 227/176.1 |
| 2014/0001235 A1* | 1/2014 | Shelton, IV | A61B 34/37 227/176.1 |
| 2014/0005678 A1* | 1/2014 | Shelton, IV | A61B 17/07207 606/130 |
| 2014/0005718 A1* | 1/2014 | Shelton, IV | A61B 17/07207 606/205 |
| 2014/0276761 A1 | 9/2014 | Parihar et al. | |
| 2014/0276948 A1* | 9/2014 | Zirps | A61B 34/73 606/130 |
| 2015/0051618 A1* | 2/2015 | Anderson | A61B 17/28 606/130 |
| 2015/0051619 A1* | 2/2015 | Cooper | A61B 17/28 606/130 |
| 2015/0053737 A1* | 2/2015 | Leimbach | A61B 90/96 227/175.1 |
| 2015/0257841 A1* | 9/2015 | Dachs, II | A61B 90/361 606/130 |
| 2015/0313676 A1 | 11/2015 | Deodhar | |
| 2016/0287252 A1 | 10/2016 | Parihar | |
| 2017/0135695 A1 | 5/2017 | Shelton et al. | |
| 2017/0252096 A1 | 9/2017 | Felder et al. | |
| 2019/0059986 A1* | 2/2019 | Shelton, IV | A61B 18/1445 |
| 2019/0282328 A1* | 9/2019 | Anderson | A61B 34/70 |
| 2019/0343525 A1* | 11/2019 | Shelton, IV | A61B 50/20 |

* cited by examiner

ROBOTIC SURGICAL TOOL WITH MANUAL RELEASE LEVER

BACKGROUND

Minimally invasive surgical (MIS) instruments are often preferred over traditional open surgical devices due to reduced post-operative recovery time and minimal scarring. Endoscopic surgery is one type of MIS procedure in which an elongate flexible shaft is introduced into the body of a patient through a natural orifice. Laparoscopic surgery is another type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The trocar also helps facilitate insufflation to elevate the abdominal wall above the organs. The instruments and tools introduced into the abdominal cavity via the trocar can be used to engage and/or treat tissue in a number of ways to achieve a diagnostic or therapeutic effect.

Various robotic systems have recently been developed to assist in MIS procedures. Robotic systems can allow for more intuitive hand movements by maintaining natural eye-hand axis. Robotic systems can also allow for more degrees of freedom in movement by including a "wrist" joint that creates a more natural hand-like articulation. The instrument's end effector can be articulated (moved) using a cable driven motion system having one or more drive cables that extend through the wrist joint.

A user (e.g., a surgeon) is able to remotely operate an instrument's end effector by grasping and manipulating in space one or more controllers that communicate with a tool driver coupled to the surgical instrument. User inputs are processed by a computer system incorporated into the robotic surgical system and the tool driver responds by actuating the cable driven motion system and, more particularly, the drive cables. Moving the drive cables articulates the end effector to desired positions and configurations.

Various types of end effectors, such as tissue graspers, forceps, needle drivers, and scissors, etc., have opposing jaws designed to open and close for a variety of reasons. In cable driven motion systems, the jaws of such end effectors open and close based on drive cable actuation (movement). In some applications, such end effectors can also incorporate electrocauterizing capabilities to simultaneously cauterize cut tissue.

Since robotic surgical systems operate based on electricity, it may be beneficial to incorporate a failsafe device that can be manually triggered without electrical input. This may prove advantageous, for example, in the event of an electrical disruption that renders the robotic surgical system inoperable. In such a scenario, a failsafe device might allow a user to manually articulate an end effector to safely release and remove the end effector from patient proximity.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to robotic surgical systems and, more particularly, to a failsafe device that allows a user to manually override articulation of an end effector used in robotic surgery.

Figure 1:
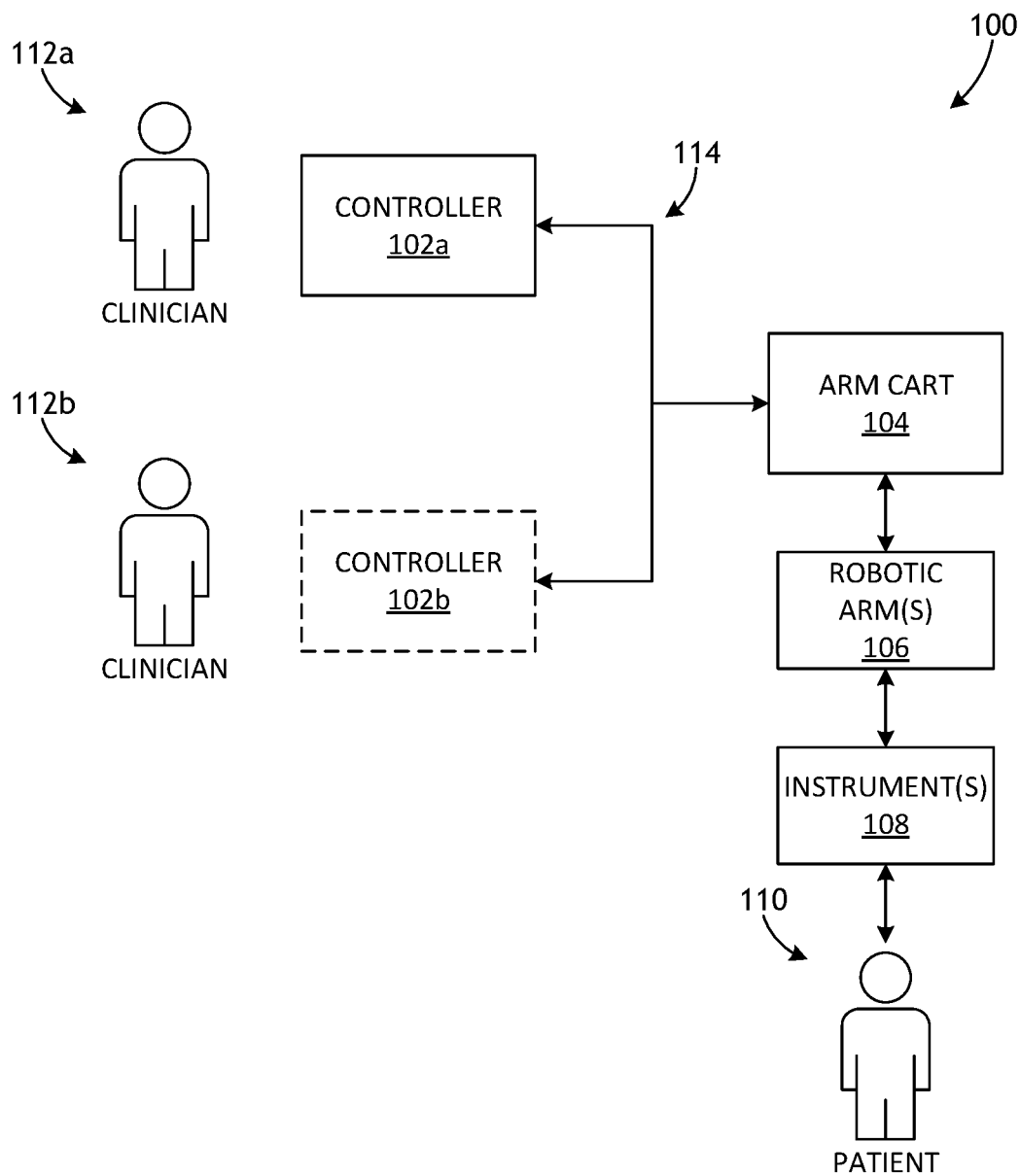
FIG. 1 is a block diagram of an example robotic surgical system that may incorporate some or all of the principles of the present disclosure.

Embodiments discussed herein describe a failsafe device that can include a manual release assembly incorporated into a surgical tool. The manual release assembly gives a user the ability to manually release an end effector in the event the robotic surgical system becomes inoperable. One example surgical tool includes a drive housing that houses drive cable capstans operatively coupled to corresponding drive inputs, an elongate shaft that extends from the drive housing, and an end effector operatively coupled to a distal end of the elongate shaft. A plurality of drive cables extend between the drive housing and the end effector, and each drive cable is associated with a corresponding one of drive cable capstans. A manual release assembly is coupled to the drive housing and includes a release lever that is manually movable between a stowed position, where the drive cable capstans are operatively coupled to the drive inputs, to an actuated position, where the drive cable capstans are disengaged from the plurality of drive inputs. Moving the release lever to the actuated position also rotates the drive cable capstans to manually articulate the end effector FIGS. 1-5 illustrate the structure and operation of example robotic surgical systems and components thereof. FIG. 1 is a block diagram of an example robotic surgical system 100 that may incorporate some or all of the principles of the present disclosure. As illustrated, the system 100 can include at least one master controller 102*a* and at least one arm cart 104. The arm cart 104 may be mechanically and/or electrically coupled to one or more robotic arms 106, alternately referred to as "tool drivers". Each robotic arm 106 may include and otherwise mount one or more surgical tools or instruments 108 for performing various surgical tasks on a patient 110. Operation of the arm cart 104, including the arms 106 and instruments 108 may be directed by a clinician 112a (e.g., a surgeon) from the master controller 102a.

In some embodiments, a second master controller 102b (shown in dashed lines) operated by a second clinician 112b may also direct operation of the arm cart 104 in conjunction with the first clinician 112a. In such embodiments, for example, each clinician 112a,b may control different arms 106 of the arm cart 104 or, in some cases, complete control of the arm cart 104 may be passed between the clinicians 112a,b. In some embodiments, additional arm carts (not shown) may be utilized on the patient 110, and these additional arm carts may be controlled by one or more of the master controllers 102a,b.

The arm cart(s) 104 and the master controllers 102a,b may be in communication with one another via a communications link 114, which may be any type of wired or wireless communications link configured to carry suitable types of signals (e.g., electrical, optical, infrared, etc.) according to any communications protocol. The communications link 114 may be an actual physical link or it may be a logical link that uses one or more actual physical links. When the link is a logical link the type of physical link may be a data link, uplink, downlink, fiber optic link, point-to-point link, for example, as is well known in the computer networking art to refer to the communications facilities that connect nodes of a network. Example implementations of robotic surgical systems, such as the system 100, are disclosed in U.S. Pat. No. 7,524,320, the contents of which are incorporated herein by reference. The various particularities of such devices will not be described in detail herein beyond that which may be necessary to understand various embodiments and forms of the various embodiments of robotic surgery apparatus, systems, and methods disclosed herein.

Figure 2:
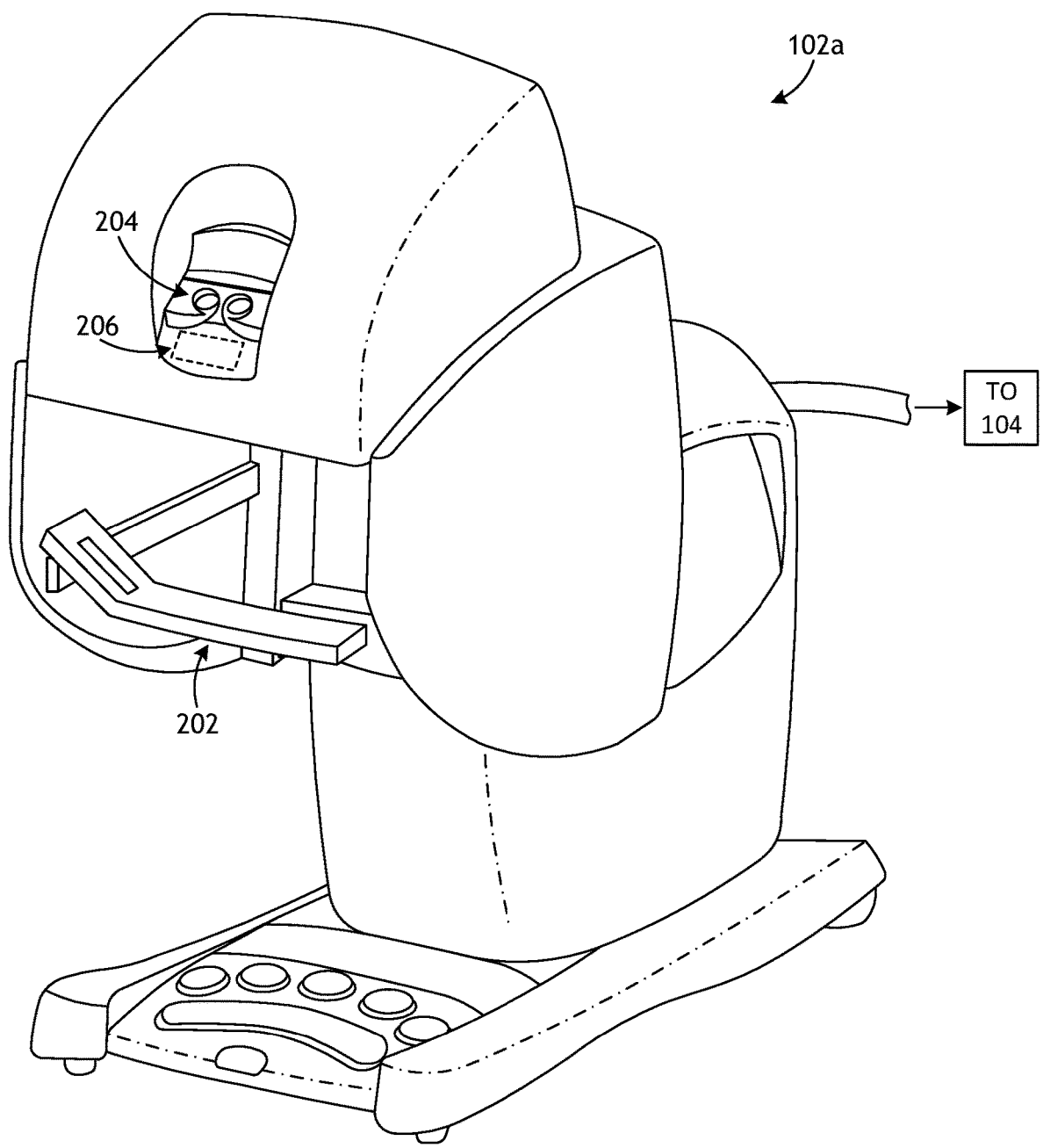
FIG. 2 is an example embodiment of the master controller of FIG. 1 that may be used to operate a robotic arm slave cart.

FIG. 2 is an example embodiment of the master controller 102a that may be used to operate a robotic arm slave cart, such as the arm cart 104 of FIG. 1. The master controller 102a and its associated arm cart 104, as well as their respective components and control systems, are collectively referred to herein as a "robotic surgical system." Examples of such systems and devices are disclosed in U.S. Pat. No. 7,524,320 and, therefore, will not be described in detail herein beyond that which may be necessary to understand various embodiments and forms of the present invention.

The master controller 102a generally includes one or more controllers 202 that can be grasped by a surgeon (e.g., the clinician 112a of FIG. 1) and manipulated in space while the surgeon views the procedure via a stereo display 204. The master controllers 202 generally comprise manual input devices designed to move in multiple degrees of freedom, and which often further have an actuatable handle for actuating a surgical instrument (e.g., the surgical instrument(s) 108 of FIG. 1), for example, for opening and closing opposing jaws, applying an electrical potential (current) to an electrode, or the like.

In the illustrated example, the master controller 102a further includes an optional feedback meter 206 viewable by the surgeon via the display 204 to provide the surgeon with a visual indication of the amount of force being applied to the surgical instrument (i.e., a cutting instrument or dynamic clamping member). Other sensor arrangements may be employed to provide the master controller 102a with an indication of other surgical instrument metrics, such as whether a staple cartridge has been loaded into an end effector or whether an anvil has been moved to a closed position prior to firing, for example.

Figure 3:
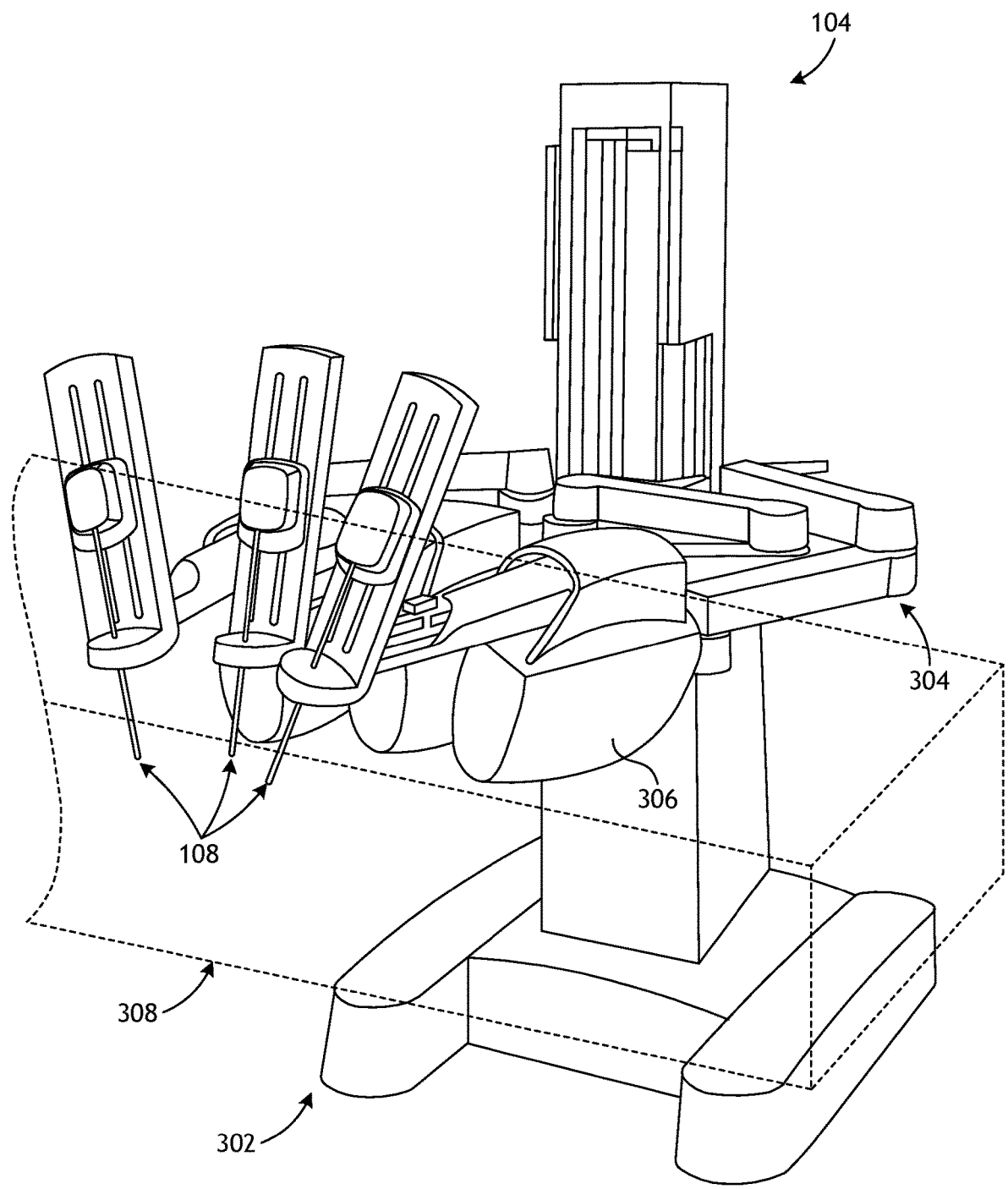
FIG. 3 depicts an example embodiment of the robotic arm cart of FIG. 1 used to actuate a plurality of surgical instruments.

FIG. 3 depicts an example embodiment of the robotic arm cart 104 used to actuate a plurality of surgical instruments 108, alternately referred to as "surgical tools." Various robotic surgery systems and methods employing master controller and robotic arm cart arrangements are described in U.S. Pat. No. 6,132,368, the contents of which are hereby incorporated by reference. As illustrated, the robotic arm cart 104 may include a base 302 that supports three surgical instruments 108, and the surgical instruments 108 are each supported by a series of manually articulatable linkages, generally referred to as set-up joints 304, and a robotic manipulator 306. These structures are herein illustrated with protective covers extending over much of the robotic linkage. These protective covers may be optional, and may be limited in size or entirely eliminated in some embodiments to minimize the inertia that is encountered by the servo mechanisms used to manipulate such devices, to limit the volume of moving components so as to avoid collisions, and to limit the overall weight of the cart 104.

The cart 104 will generally have dimensions suitable for transporting the cart 104 between operating rooms. The cart 104 may be configured to fit through standard operating room doors and onto standard hospital elevators. In some embodiments, the cart 104 may include a wheel system (or other transportation system) that allows the cart 104 to be positioned adjacent an operating table by a single attendant. In various embodiments, an automated reloading system including a base portion may be strategically located within a work envelope 308 of the robotic arm cart 104.

Figure 4:
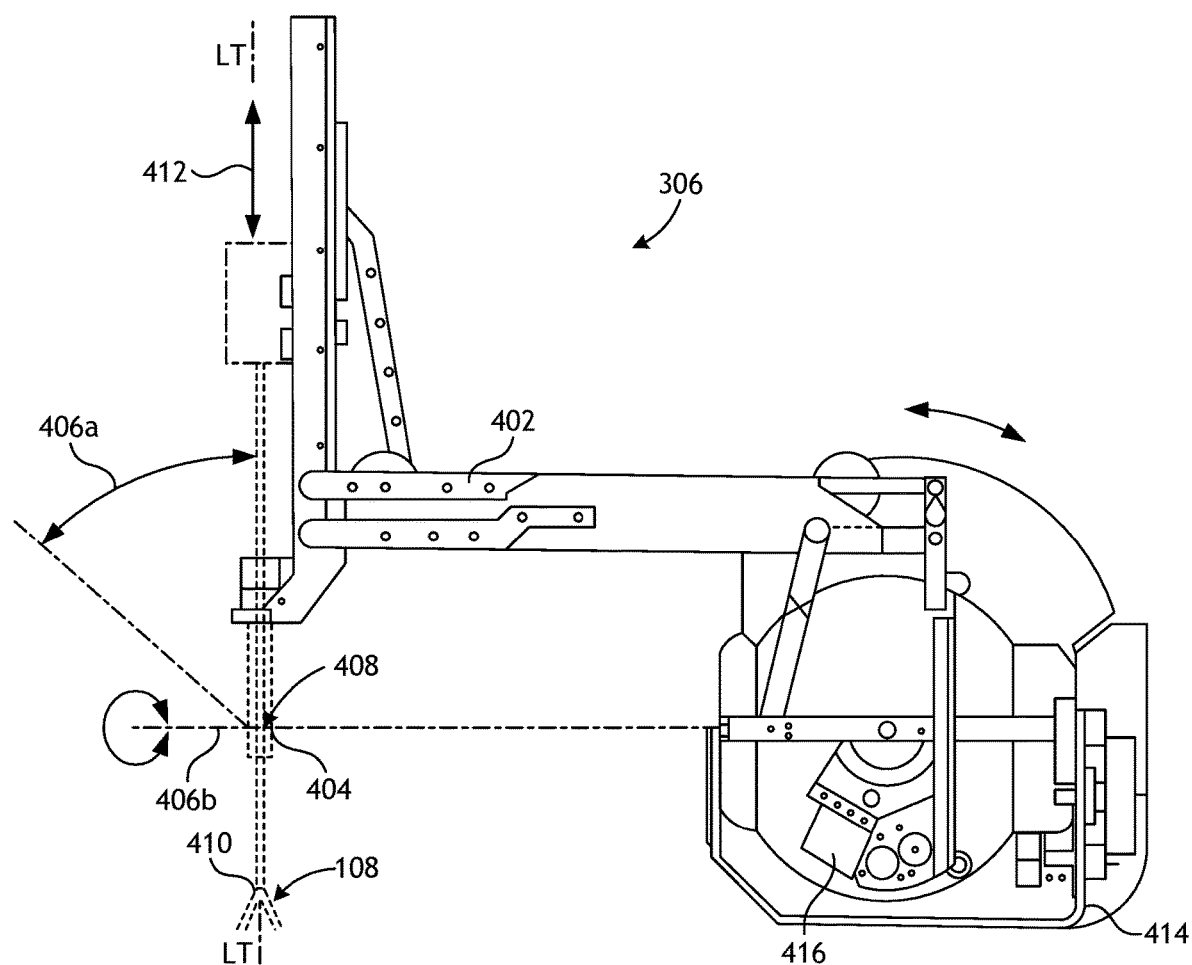
FIG. 4 is a side view schematic diagram of an example embodiment of the robotic manipulator of FIG. 3.

FIG. 4 is a side view schematic diagram of an example embodiment of the robotic manipulator 306. As illustrated, the robotic manipulator 306 may include linkage 402 that constrains movement of the surgical instrument 108 coupled thereto. The linkage 402 includes rigid links coupled by rotational joints in a parallelogram arrangement so that the surgical instrument 108 rotates around a point 404 in space.

The parallelogram arrangement constrains rotation to pivoting about a "pitch axis" that extends axis through the point 404, as indicated by a pitch arrow 406a. The links supporting the parallelogram linkage 402 are pivotally mounted to set-up joints 304 (FIG. 3) so that the surgical instrument 108 further rotates about a second axis 406b, referred to as the "yaw axis." The pitch axis and the yaw axis 406b intersect at a remote center 408, which is aligned along a shaft 410 of the surgical instrument 108.

The surgical instrument 108 may have further degrees of driven freedom as supported by the robotic manipulator 306, including sliding motion of the surgical instrument 108 along a longitudinal tool axis "LT-LT". As the surgical instrument 108 slides (translates) along the longitudinal tool axis LT-LT relative to the robotic manipulator 306 (arrow 412), the remote center 408 remains fixed relative to a base 414 of the robotic manipulator 306. Hence, the entire robotic manipulator 306 is generally moved to re-position the remote center 408.

The linkage 402 of the robotic manipulator 306 is driven by a series of motors 416. These motors 416 actively move the linkage 402 in response to commands from a processor of a control system. The motors 416 may also be employed to manipulate the surgical instrument 108.

Figure 5:
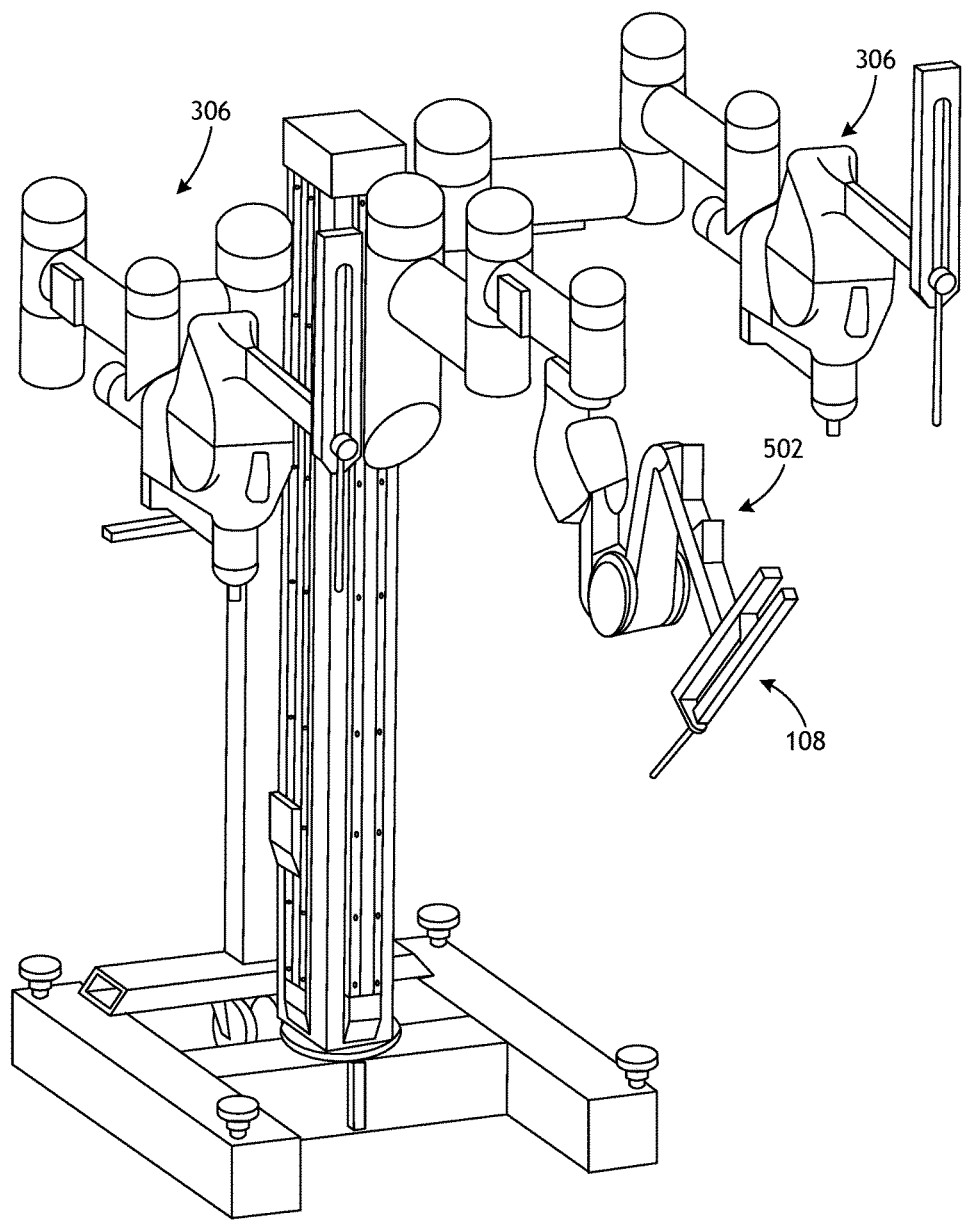
FIG. 5 is a perspective view of an alternative example robotic manipulator.

FIG. 5 is a perspective view of an alternative example robotic manipulator 502, used in conjunction with two robotic manipulators similar to the robotic manipulators 306 described in FIG. 4. As illustrated, a surgical instrument 108 is supported by the robotic manipulator 502 between the two robotic manipulators 306 generally described above. Those of ordinary skill in the art will appreciate that various embodiments of the present invention may incorporate a wide variety of alternative robotic structures, including those described in U.S. Pat. No. 5,878,193, the contents of which are hereby incorporated by reference. Additionally, while the data communication between a robotic component and the processor of the robotic surgical system is primarily described herein with reference to communication between the surgical instrument 108 and the master controller 102*a* (FIG. 2), it should be understood that similar communication may take place between circuitry of a robotic manipulator, a set-up joint, an endoscope or other image capture device, or the like, and the processor of the robotic surgical system for component compatibility verification, component-type identification, component calibration (such as off-set or the like) communication, confirmation of coupling of the component to the robotic surgical system, or the like.

Figure 6:
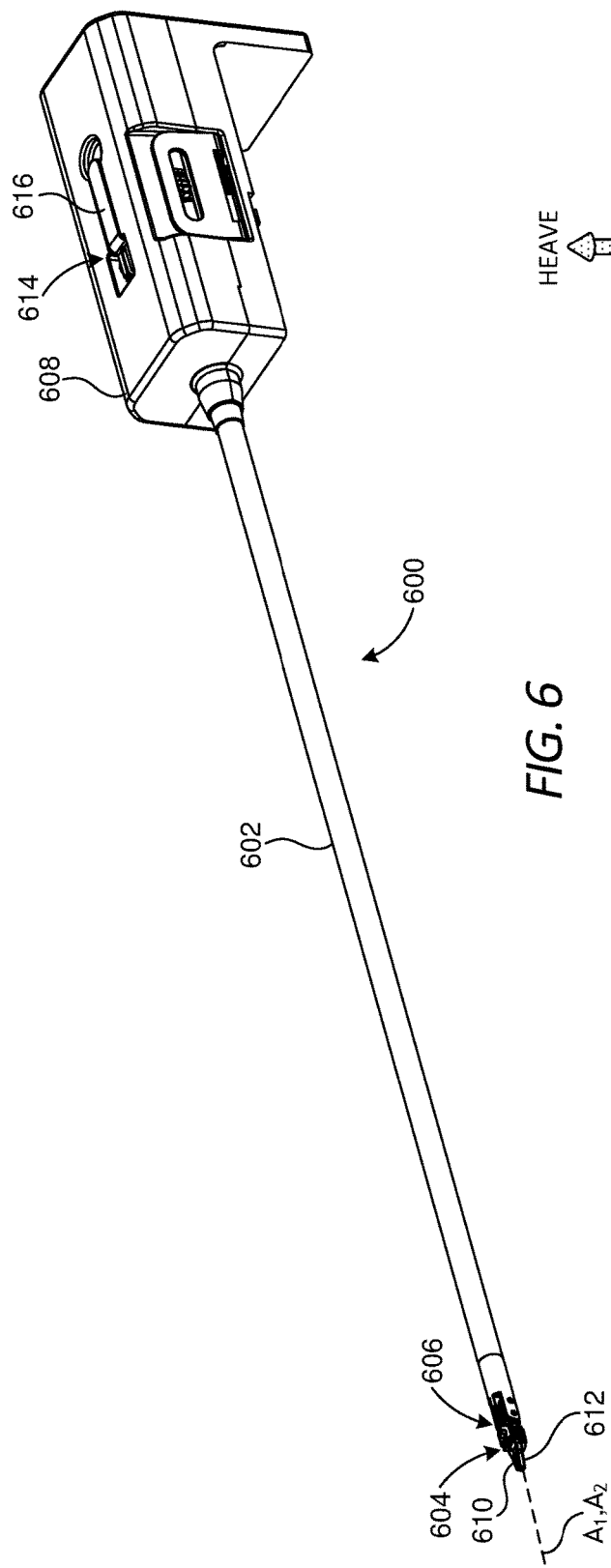
FIG. 6 is a side view of an example surgical tool that may incorporate some or all of the principles of the present disclosure.

FIG. 6 is side view of an example surgical tool 600 that may incorporate some or all of the principles of the present disclosure. The surgical tool 600 may be the same as or similar to the surgical instrument(s) 108 of FIGS. 1 and 3-5) and, therefore, may be used in conjunction with a robotic surgical system, such as the robotic surgical system 100 of FIG. 1. Accordingly, the surgical tool 600 may be designed to be releasably coupled to a tool driver included in the robotic surgical system 100.

As illustrated, the surgical tool 600 includes an elongate shaft 602, an end effector 604, a wrist 606 (alternately referred to as a "wrist joint") that couples the end effector 604 to the distal end of the shaft 602, and a drive housing 608 coupled to the proximal end of the shaft 602. In applications where the surgical tool is used in conjunction with a robotic surgical system (e.g., the robotic surgical system 100 of FIG. 1), the drive housing 608 can include coupling features that releasably couple the surgical tool 600 to the robotic surgical system.

The terms "proximal" and "distal" are defined herein relative to a robotic surgical system having an interface configured to mechanically and electrically couple the surgical tool 600 (e.g., the housing 608) to a robotic manipulator. The term "proximal" refers to the position of an element closer to the robotic manipulator and the term "distal" refers to the position of an element closer to the end effector 604 and thus further away from the robotic manipulator. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 600, the end effector 604 is configured to move (pivot) relative to the shaft 602 at the wrist 606 to position the end effector 604 at desired orientations and locations relative to a surgical site. The housing 608 includes (contains) various mechanisms designed to control operation of various features associated with the end effector 604 (e.g., clamping, firing, rotation, articulation, energy delivery, etc.). In at least some embodiments, the shaft 602, and hence the end effector 604 coupled thereto, is configured to rotate about a longitudinal axis $A_1$ of the shaft 602. In such embodiments, at least one of the mechanisms included (housed) in the housing 608 is configured to control rotational movement of the shaft 602 about the longitudinal axis $A_1$.

The surgical tool 600 can have any of a variety of configurations capable of performing at least one surgical function. For example, the surgical tool 600 may include, but is not limited to, forceps, a grasper, a needle driver, scissors, an electro cautery tool, a stapler, a clip applier, a suction tool, an irrigation tool, an imaging device (e.g., an endoscope or ultrasonic probe), or any combination thereof. In some embodiments, the surgical tool 600 may be configured to apply energy to tissue, such as radiofrequency (RF) energy.

The shaft 602 is an elongate member extending distally from the housing 608 and has at least one lumen extending therethrough along its axial length. In some embodiments, the shaft 602 may be fixed to the housing 608, but could alternatively be rotatably mounted to the housing 608 to allow the shaft 602 to rotate about the longitudinal axis $A_1$. In yet other embodiments, the shaft 602 may be releasably coupled to the housing 608, which may allow a single housing 608 to be adaptable to various shafts having different end effectors.

The end effector 604 can have a variety of sizes, shapes, and configurations. In the illustrated embodiment, the end effector 604 includes opposing jaws 610, 612 configured to move (articulate) between open and closed positions. Accordingly, the end effector 604 can comprise, but is not limited to, a tissue grasper, a clip applier, scissors, a needle driver, a babcock including a pair of opposed grasping jaws, or any other surgical tool that incorporates opposing jaws. One or both of the jaws 610, 612 may be configured to pivot at the wrist 606 to articulate the end effector 604 between the open and closed positions.

Figure 7:
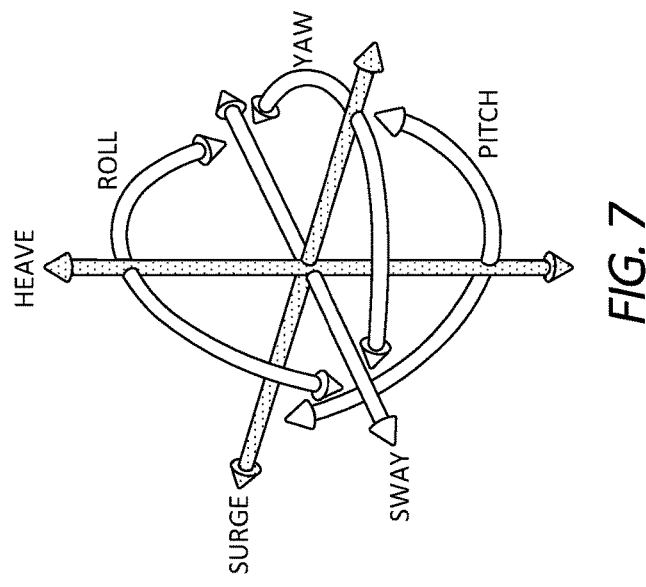
FIG. 7 illustrates potential degrees of freedom in which the wrist of FIG. 1 may be able to articulate (pivot).

FIG. 7 illustrates the potential degrees of freedom in which the wrist 606 may be able to articulate (pivot). The wrist 606 can have any of a variety of configurations. In general, the wrist 606 comprises a joint configured to allow pivoting movement of the end effector 604 relative to the shaft 602. The degrees of freedom of the wrist 606 are represented by three translational variables (i.e., surge, heave, and sway), and by three rotational variables (i.e., Euler angles or roll, pitch, and yaw). The translational and rotational variables describe the position and orientation of a component of a surgical system (e.g., the end effector 604) with respect to a given reference Cartesian frame. As depicted in FIG. 7, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 606 (e.g., X-axis), yaw movement about a second axis of the wrist 606 (e.g., Y-axis), and combinations thereof to allow for 360° rotational movement of the end effector 604 about the wrist 606. In other applications, the pivoting motion can be limited to movement in a single plane, e.g., only pitch movement about the first axis of the wrist 606 or only yaw movement about the second axis of the wrist 606, such that the end effector 604 moves only in a single plane.

Referring again to FIG. 6, the surgical tool 600 includes a plurality of drive cables (obscured in FIG. 6) that form part of a cable driven motion system configured to facilitate movement of (articulate) the end effector 604 relative to the shaft 602. Moving the drive cables moves the end effector 604 between an unarticulated position and an articulated position. The end effector 604 is depicted in FIG. 6 in the unarticulated position where a longitudinal axis $A_2$ of the end effector 604 is substantially aligned with the longitudinal axis $A_1$ of the shaft 602, such that the end effector 604 is at a substantially zero angle relative to the shaft 602. Due to factors such as manufacturing tolerance and precision of measurement devices, the end effector 604 may not be at a precise zero angle relative to the shaft 602 in the unarticulated position, but nevertheless be considered "substantially aligned" thereto. In the articulated position, the longitudinal axes $A_1$, $A_2$ would be angularly offset from each other such that the end effector 604 is at a non-zero angle relative to the shaft 602.

According to embodiments of the present disclosure, the surgical tool 600 may further include a manual release assembly 614 that may be manually actuated by a user (e.g., a surgeon) to override the cable driven system and thereby manually articulate the end effector 604. For the illustrated embodiment, employing the manual release assembly 614 would result in the jaws 610, 612 opening, which might prove beneficial in the event of an electrical disruption that renders the surgical tool 600 inoperable. In such applications, the user would be able to open the jaws 610, 612 by manually actuating the manual release assembly 614, and thereby release any grasped tissue. In other applications, the manual release assembly 614 may be actuated (enabled) to open the jaws 610, 612 in preparation for cleaning and/or sterilization of the surgical tool 600.

In the illustrated embodiment, the manual release assembly 614 includes a release lever 616. A user is able to manually grasp and lift the release lever 616 from a stowed position, as shown, to an actuated position. When the release lever 616 is in the stowed position, the surgical tool 600 is able to operate as normal. However, as the release lever 616 is lifted and moved to the actuated position, various internal component parts of the manual release assembly 614 housed within the drive housing 608 are simultaneously moved, which result in manual articulation of the end effector 604.

It should be noted that while the release lever 616 is depicted in FIG. 6 as being accessible via a top surface of the drive housing 608, the position of the release lever 616 is just one example and should not be considered limiting to the scope of the present disclosure. Moreover, the release lever 616 is just one example of a means to manually enable (actuate) the manual release assembly 614 and, therefore, should not be considered limiting to the scope of the present disclosure.

Figure 8:
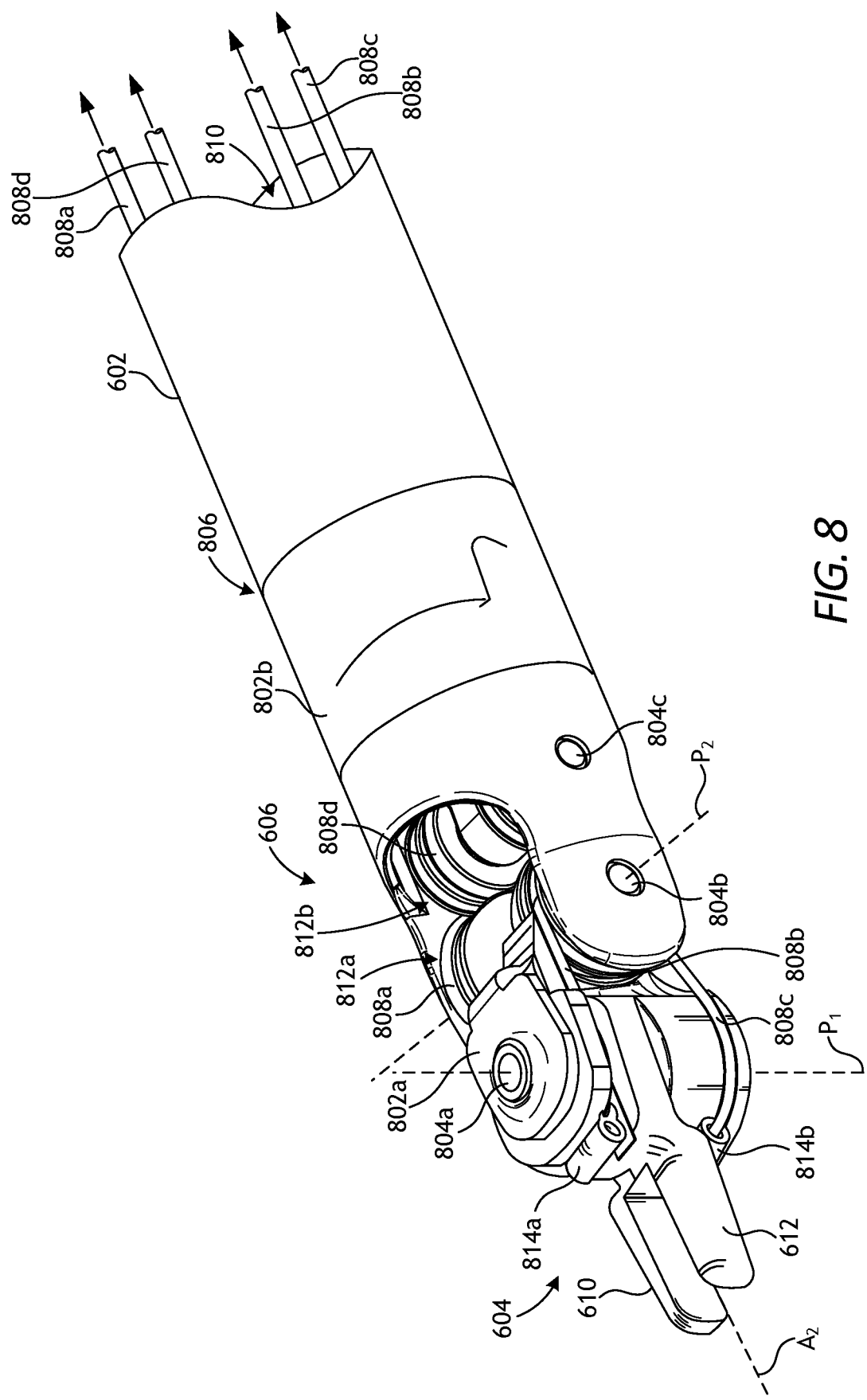
FIG. 8 is an enlarged isometric view of the distal end of the surgical tool of FIG. 1.

FIG. 8 is an enlarged isometric view of the distal end of the surgical tool 600 of FIG. 6. More specifically, FIG. 8 depicts enlarged views of the end effector 604 and the wrist 606, with the end effector 604 in an unarticulated position where the jaws 610, 612 are closed. The wrist 606 operatively couples the end effector 604 to the shaft 602. To accomplish this, the wrist 606 includes a distal clevis 802a and a proximal clevis 802b. The end effector 604 (i.e., the jaws 610, 612) is rotatably mounted to the distal clevis 802a at a first axle 804a, the distal clevis 802a is rotatably mounted to the proximal clevis 802b at a second axle 804b, and the proximal clevis 802b is coupled to a distal end 806 of the shaft 602.

The wrist 606 provides a first pivot axis $P_1$ that extends through the first axle 804a and a second pivot axis $P_2$ that extends through the second axle 804b. The first pivot axis $P_1$ is substantially perpendicular (orthogonal) to the longitudinal axis $A_2$ of the end effector 604, and the second pivot axis $P_2$ is substantially perpendicular (orthogonal) to both the longitudinal axis $A_2$ and the first pivot axis $P_1$. Movement about the first pivot axis $P_1$ provides "yaw" articulation of the end effector 604, and movement about the second pivot axis $P_2$ provides "pitch" articulation of the end effector 604. In the illustrated embodiment, the jaws 610, 612 are mounted at the first pivot axis $P_1$, thereby allowing the jaws 610, 612 to pivot relative to each other to open and close the end effector 604 or alternatively pivot in tandem to articulate the orientation of the end effector 604.

A plurality of drive cables 808, shown as drive cables 808a, 808b, 808c, and 808d, extend longitudinally within a lumen 810 defined by the shaft 602 and pass through the wrist 606 to be operatively coupled to the end effector 604. The drive cables 808a-d form part of the cable driven motion system briefly described above, and may be referred to and otherwise characterized as cables, bands, lines, cords, wires, ropes, strings, twisted strings, elongate members, etc. The drive cables 808a-d can be made from a variety of materials including, but not limited to, metal (e.g., tungsten, stainless steel, etc.) or a polymer. Example drive cables are described in U.S. Patent Pub. No. 2015/0209965 entitled "Compact Robotic Wrist," and U.S. Patent Pub. No. 2015/0025549 entitled "Hyperdexterous Surgical System," the contents of which are hereby incorporated by reference. The lumen 810 can be a single lumen, as illustrated, or can alternatively comprise a plurality of independent lumens that each receive one or more of the drive cables 808a-d.

The drive cables 808a-d extend proximally from the end effector 604 to the drive housing 608 (FIG. 6) where they are operatively coupled to various actuation mechanisms or devices housed (contained) therein to facilitate longitudinal movement (translation) of the drive cables 808a-d within the lumen 810. Selective actuation of all or a portion of the drive cables 808a-d causes the end effector 604 (e.g., one or both of the jaws 610, 612) to articulate (pivot) relative to the shaft 602. More specifically, selective actuation causes a corresponding drive cable 808a-d to translate longitudinally within the lumen of the shaft 602 and thereby cause pivoting movement of the end effector 604. One or more drive cables 808a-d, for example, may translate longitudinally to cause the end effector 604 to articulate (e.g., both of the jaws 610, 612 angled in a same direction), to cause the end effector 604 to open (e.g., one or both of the jaws 610, 612 move away from the other), or to cause the end effector 604 to close (e.g., one or both of the jaws 610, 612 move toward the other).

Moving the drive cables 808a-d can be accomplished in a variety of ways, such as by triggering an associated actuator or mechanism operatively coupled to or housed within the drive housing 608 (FIG. 6). Moving a given drive cable 808a-d constitutes applying tension (i.e., pull force) to the given drive cable 808a-d in a proximal direction, which causes the given drive cable 808a-d to translate and thereby cause the end effector 604 to move (articulate) relative to the shaft 602.

The wrist 606 includes a first plurality of pulleys 812a and a second plurality of pulleys 812b, each configured to interact with and redirect the drive cables 808a-d for engagement with the end effector 604. The first plurality of pulleys 812a is mounted to the proximal clevis 802b at the second axle 804b and the second plurality of pulleys 812b is also mounted to the proximal clevis 802b but at a third axle 804c located proximal to the second axle 804b. The first and second pluralities of pulleys 812a,b cooperatively redirect the drive cables 808a-d through an "S" shaped pathway before the drive cables 808a-d are operatively coupled to the end effector 604.

In at least one embodiment, one pair of drive cables 808a-d is operatively coupled to each jaw 610, 612 and configured to "antagonistically" operate the corresponding jaw 610, 612. In the illustrated embodiment, for example, a first connector 814a mounted to the first jaw 810 couples the first and second drive cables 808a,b, and a second connector 814b mounted to the second jaw 812 couples the third and fourth drive cables 808c,d. Actuation of the first drive cable 808a acts on the first connector 814a and thereby pivots the first jaw 810 about the first pivot axis $P_1$ toward the open position. In contrast, actuation of the second drive cable 808b also acts on the first connector 814a but pivots the first jaw 810 about the first pivot axis $P_1$ in the opposite direction and toward the closed position. Similarly, actuation of the third drive cable 808c acts on the second connector 814b and thereby pivots the second jaw 812 about the first pivot axis $P_1$ toward the open position, while actuation of the fourth drive cable 808d also acts on the second connector 814ab but pivots the second jaw 812 about the first pivot axis $P_1$ in the opposite direction and toward the closed position.

Accordingly, the drive cables 808a-d may be characterized or otherwise referred to as "antagonistic" cables that cooperatively (yet antagonistically) operate to cause relative or tandem movement of the first and second jaws 610, 612. When the first drive cable 808a is actuated (moved), the second drive cable 808b naturally follows as coupled to the first drive cable 808a at the first connector 814a, and vice versa. Similarly, when the third drive cable 808c is actuated, the fourth drive cable 808d naturally follows as coupled to the third drive cable 808c at the second connector 814b, and vice versa.

Figure 9:
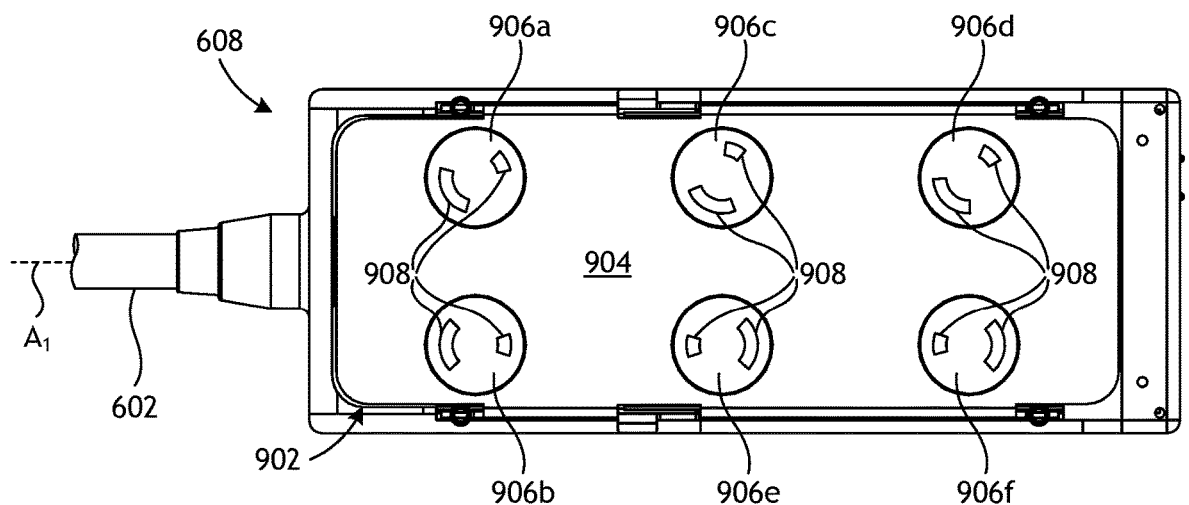
FIG. 9 is a bottom view of the drive housing of the surgical tool of FIG. 6.

FIG. 9 is a bottom view of the drive housing 608, according to one or more embodiments. As illustrated, the drive housing 608 (alternately referred to as a "puck") may include a tool mounting portion 902 used to operatively couple the drive housing 608 to a tool driver of a robotic manipulator (e.g., the robotic manipulators 306, 502 of FIGS. 3 and 5, respectively). The tool mounting portion 902 may releasably attach (couple) the drive housing 608 to a tool driver in a variety of ways, such as by clamping thereto, clipping thereto, or slidably mating therewith. In some embodiments, the tool mounting portion 902 may include an array of electrical connecting pins, which may be coupled to an electrical connection on the mounting surface of the tool driver. While the tool mounting portion 902 is described herein with reference to mechanical, electrical, and magnetic coupling elements, it should be understood that a wide variety of telemetry modalities might be used, including infrared, inductive coupling, or the like.

The tool mounting portion 902 includes and otherwise provides an interface 904 configured to mechanically, magnetically, and/or electrically couple the drive housing 608 to the tool driver. In some embodiments, as described herein, the interface 904 may also comprise a lower chassis of the drive housing 608 used to support some of the internal component parts within the drive housing 608. Accordingly, the interface 904 may alternatively be referred to herein as the "lower chassis 904."

As illustrated, the interface 904 includes and supports a plurality of drive inputs, shown as drive inputs 906a, 906b, 906c, 906d, 906e, and 906f. In at least one embodiment, each drive input 906a-f comprises a rotatable disc configured to align with and couple to a corresponding input actuator (not shown) of a given tool driver. Moreover, each drive input 906a-f provides or defines one or more surface features 908 configured to align with mating surface features provided on the corresponding input actuator. The surface features 908 can include, for example, various protrusions and/or indentations that facilitate a mating engagement. In some embodiments, some or all of the drive inputs 906a-f may include one surface feature 908 that is positioned closer to an axis of rotation of the associated drive input 906a-f than the other surface feature(s) 908. This may help to ensure positive angular alignment of each drive input 906a-f.

In some embodiments, actuation of the first drive input 906a may be configured to control rotation of the elongate shaft 602 about its longitudinal axis $A_1$. The elongate shaft 602 may be rotated clockwise or counter-clockwise depending on the rotational actuation of the first drive input 906a. In some embodiments, actuation of the second drive input 906b may be configured to control a lockout mechanism (alternately referred to as a deadbolt), which locks the end effector 604 (FIGS. 6 and 8) in a predetermined pose or position. In some embodiments, actuation of the third drive input 906c, the fourth drive input 906d, the fifth drive input 906e, and the sixth drive input 906f may be configured to operate movement (axial translation) of the drive cables 808a-d (FIG. 8), which results in the articulation of the end effector 604. Each of the drive inputs 906a-f may be actuated based on user inputs communicated to a tool driver coupled to the interface 904, and the user inputs may be received via a computer system incorporated into the robotic surgical system.

Figure 10:
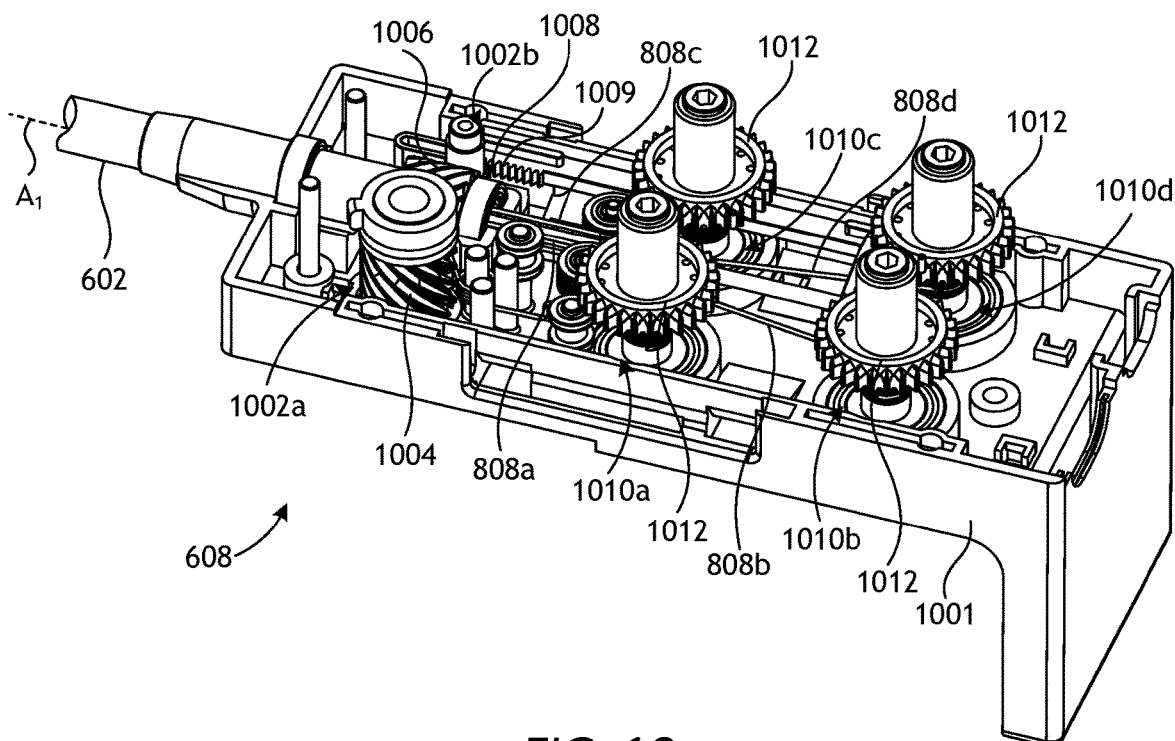
FIG. 10 is an isometric exposed view of the interior of the drive housing of the surgical tool of FIG. 6.

FIG. 10 is an isometric exposed view of the interior of the drive housing 608, according to one or more embodiments. Several component parts that may be otherwise contained within the drive housing 608 are not shown in FIG. 10 to enable discussion of the depicted component parts. The drive housing 608 includes a main body 1001 that holds and otherwise supports all of the internal component parts of the drive housing 608. As illustrated, a first capstan 1002a and a second capstan 1002b are contained (housed) within the drive housing 608. The first capstan 1002a may be operatively coupled to or extend from the first drive input 906a (FIG. 9), and the second capstan 1002b may be operatively coupled to or extend from the second drive input 906b (FIG. 9). Accordingly, actuation of the first drive input 906a results in rotation of the first capstan 1002a and actuation of the second drive input 906b results in rotation of the second capstan 1002b.

A spiral worm drive gear 1004 is coupled to or forms part of the first capstan 1002a. The spiral worm drive gear 1004 may be configured to mesh and interact with a driven gear 1006 secured within the drive housing 608 and operatively coupled to the shaft 602 such that rotation of the driven gear 1006 correspondingly rotates the shaft 602. Accordingly, rotation of the spiral worm drive gear 1004 (via actuation of the first drive input 906a of FIG. 9) will drive the driven gear 1006 and thereby control rotation of the elongate shaft 602 about the longitudinal axis $A_1$.

A spur gear 1008 may be coupled to or form part of the second capstan 1002b and configured to mesh and interact with a rack gear 1009 contained within the drive housing 608. The rack gear 1009 may be operatively coupled to a lockout mechanism (not shown) that is movable to lock the end effector 604 (FIGS. 6 and 8) in a predetermined pose or position. Accordingly, rotation of the spur gear 1008 (via actuation of the second drive input 906b of FIG. 9) will control the lockout mechanism and thereby lock and unlock the end effector 604 as desired.

The drive housing 608 further contains or houses a first drive cable capstan 1010a, a second drive cable capstan 1010b, a third drive cable capstan 1010c, and a fourth drive cable capstan 1010d. While four drive cable capstans 1010a-d are depicted in FIG. 10, alternative embodiments may include more or less than four, without departing from the scope of the disclosure. In the illustrated embodiment, the first drive cable capstan 1010a is operatively coupled to or extends from the third drive input 906c (FIG. 9), the second drive cable capstan 1010b is operatively coupled to or extends from the fourth drive input 906d (FIG. 9), the third drive cable capstan 1010c is operatively coupled to or extends from the fifth drive input 906e (FIG. 9), and the fourth drive cable capstan 1010d is operatively coupled to or extends from the sixth drive input 906f (FIG. 9). Accordingly, actuation of the third drive input 906c results in rotation of the first drive cable capstan 1010a, actuation of the fourth drive input 906d results in rotation of the second drive cable capstan 1010b, actuation of the fifth drive input 906e results in rotation of the third drive cable capstan 1010c, and actuation of the sixth drive input 906f results in rotation of the fourth drive cable capstan 1010d.

Each drive cable capstan 1010a-d is configured to be operatively coupled to a corresponding one of the drive cables 808a-d such that rotation of a given drive cable capstan 1010a-d actuates (longitudinally moves) a corresponding one of the drive cables 808a-d. More specifically, rotation of the first drive cable capstan 1010a (via actuation of the third drive input 906c of FIG. 9) will control movement of the first drive cable 808a; rotation of the second drive cable capstan 1010b (via actuation of the fourth drive input 906d of FIG. 9) will control movement of the second drive cable 808b; rotation of the third drive cable capstan 1010c (via actuation of the fifth drive input 906e of FIG. 9) will control movement of the third drive cable 808c; and rotation of the fourth drive cable capstan 1010d (via actuation of the sixth drive input 906f of FIG. 9) will control movement of the fourth drive cable 808d.

Each drive cable capstan 1010a-d has a corresponding spur gear 1012 coupled thereto such that rotation of a given drive cable capstan 1010a-d will rotate the corresponding spur gear 1012 in the same angular direction. The spur gears 1012 form part of the manual release assembly 614 (FIG. 6) of the present disclosure. As described below, when the manual release assembly 614 is actuated, the drive cable capstans 1010a-d disengage from the drive inputs 906c-f (FIG. 9) and one or more of the spur gears 1012 may be reverse rotated to manually articulate the end effector 604 (FIGS. 6 and 8).

Figure 11:
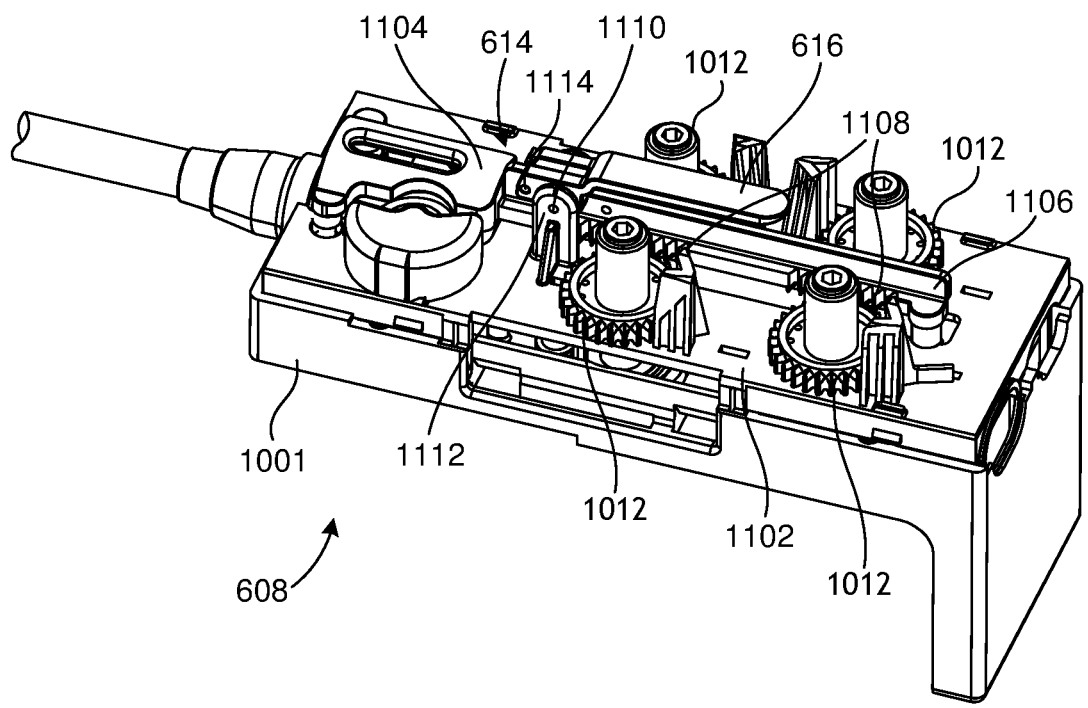
FIG. 11 is another isometric exposed view of the interior of the drive housing showing the component parts of the manual release assembly.

FIG. 11 is another isometric exposed view of the interior of the drive housing 608, now showing the component parts of the manual release assembly 614, according to one or more embodiments. As illustrated, the drive housing 608 includes an upper chassis 1102 positioned within the drive housing 608 and configured to support the manual release assembly 614. The manual release assembly 614 includes a jaw release frame 1104 that includes or otherwise provides a gear rack 1106 that extends longitudinally within the housing 608. The gear rack 1106 may provide one or more rack gears 1108 (two shown) configured to mesh and interact with two or more of the spur gears 1012 coupled to each drive cable capstan 1010a-d. While not visible in FIG. 11, the gear rack 1106 may include one or more additional rack gears 1108 arranged on the opposite side and configured to mesh and interact with the laterally adjacent spur gears 1012.

The release lever 616 is rotatably coupled to the upper chassis 1102 at a first pin 1110. More specifically, the upper chassis 1102 may provide a support 1112 configured to receive and rotatably mount the release lever 616. The first pin 1110 extends through the support 1112 and the release lever 616 to provide a pivot point about which the release lever 616 may rotate relative to the upper chassis 1102 between stowed and actuated positions. In the illustrated embodiment, the support 1112 is in the form of a clevis that receives the release lever 616, but could alternatively comprise any other type of support structure capable of rotatably mounting the release lever 616 to the upper chassis 1102.

The release lever 616 may also be movably coupled to the jaw release frame 1104 at a second pin 1114. As described in more detail below, the release lever 616 may be actuated from its stowed position by manually rotating (pivoting) the release lever 616 about the first pin 1110, which will cause the jaw release frame 1104 to correspondingly move as coupled to the release lever 616 at the second pin 1114. Moving the jaw release frame 1104 as acted upon by the release lever 616 will position the rack gears 1108 to mesh with the laterally adjacent spur gears 1012. As the release lever 616 continues to rotate (pivot) toward its actuated position, the rack gears 1108 will translate longitudinally and simultaneously reverse rotate the laterally adjacent spur gears 1012, which results in manual articulation of the end effector 604 (FIGS. 6 and 8).

Figure 12A:
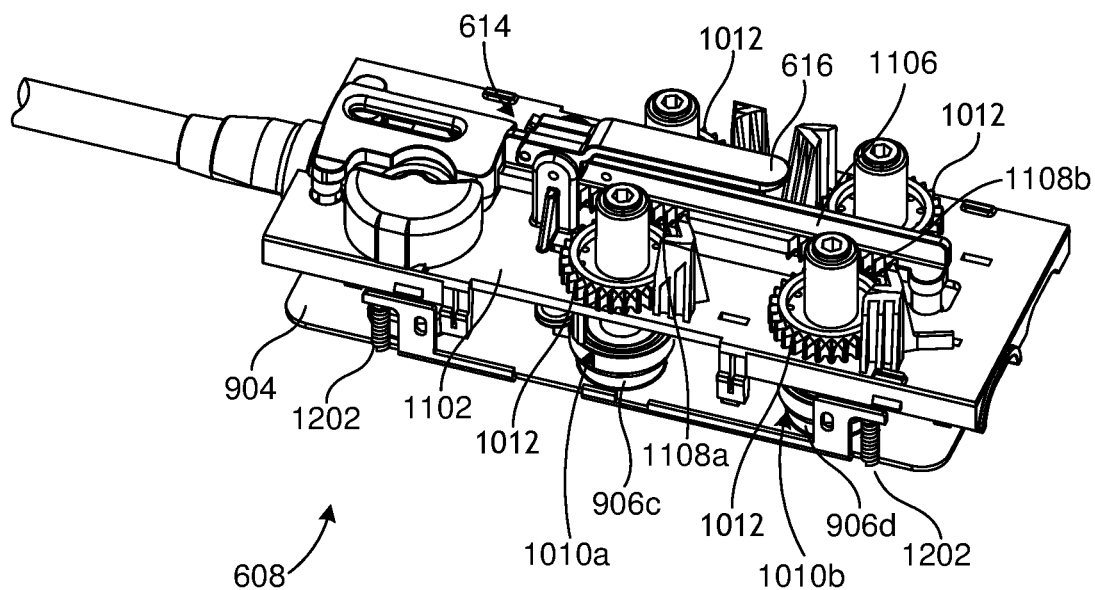
FIGS. 12A and 12B are additional isometric exposed views of the interior of the drive housing.
Figure 12B:
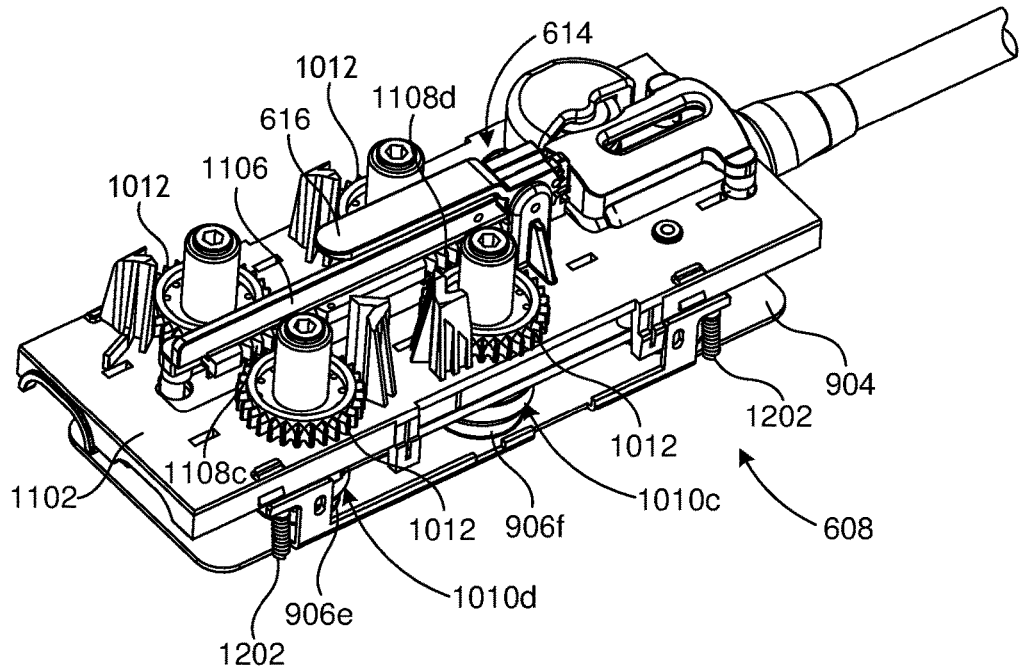

FIGS. 12A and 12B are additional isometric exposed views of the interior of the drive housing 608. The gear rack 1106 includes first and second rack gears 1108a and 1108b, as shown in FIG. 12A, and third and fourth rack gears 1108c and 1108d, as shown in FIG. 12B. While four rack gears 1108a-d are shown in FIGS. 12A and 12B, it is contemplated herein to combine the first and second rack gears 1108a,b and combine the third and fourth rack gears 1108c,d such that only two rack gears on opposing lateral sides of the gear rack 1106 are used to mesh and interact with each of the spur gears 1012. In other embodiments, however, only one or two rack gears on one lateral side of the gear rack 1106 may be utilized, without departing from the scope of the disclosure. In such embodiments, for example, only the first and second rack gears 1108a,b (or a combination thereof) may be provided, or only the third and fourth rack gears 1108c,d (or a combination thereof) may be provided. The one or two rack gears may be configured to mesh and interact with the two laterally adjacent spur gears 1012. In such embodiments, manually actuating the release lever 616 would position the rack gear(s) to engage two spur gears 1012, and thereby manually articulate only one of the jaws 610, 612 (FIGS. 6 and 8) of the end effector 604 (FIGS. 6 and 8).

FIGS. 12A and 12B also depict the lower chassis 904 (referred to in FIG. 9 as "the interface 904"). The lower chassis 904 may be compliantly coupled to the underside of the main body 1001 (FIGS. 10 and 11) of the drive housing 608. More particularly, a plurality of biasing elements 1202 may interpose the lower chassis 904 and corresponding portions of the main body 1001 and allow the upper chassis 1102 to move relative to the lower chassis 904 upon actuation of the manual release assembly 614. As discussed in more detail below, actuating the manual release assembly 614 moves the upper chassis 1102 away from the lower chassis 904, thereby disengaging the drive inputs 906c-f from the drive cable capstans 1010a-d. As will be appreciated, disengaging the drive inputs 906c-f from the drive cable capstans 1010a-d allows the spur gears 1012 to be reverse rotated to manually articulate the end effector 604 (FIGS. 6 and 8).

The drive cable capstans 1010a-d may subsequently be re-engaged with the corresponding drive inputs 906c-f by rotating (pivoting) the release lever 616 back to the stowed position. While pivoting back to the stowed position, the biasing elements 1202 may urge the upper chassis 1102 to move back to its original position, which brings the drive cable capstans 1010*a-d* into engagement once again with the drive inputs 906*c-f*. In the illustrated embodiment, the biasing elements 1202 are depicted as coil springs, but could alternatively comprise any device capable of providing a spring force between the lower chassis 904 and the upper chassis 1102.

Figure 13A:
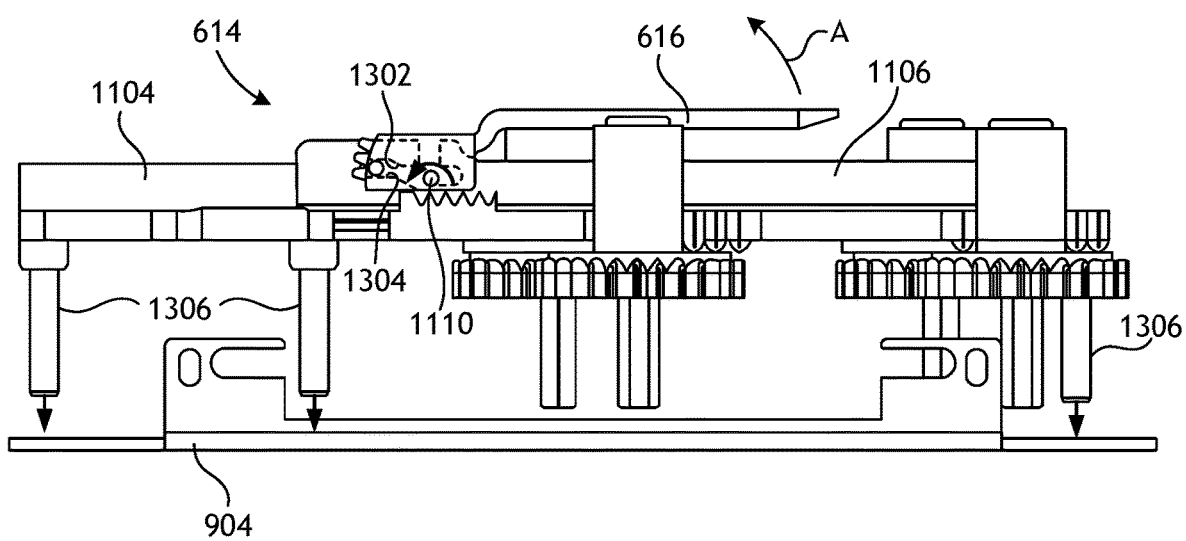
FIGS. 13A-13C are progressive side views of the manual release assembly during example operation.
Figure 13B:
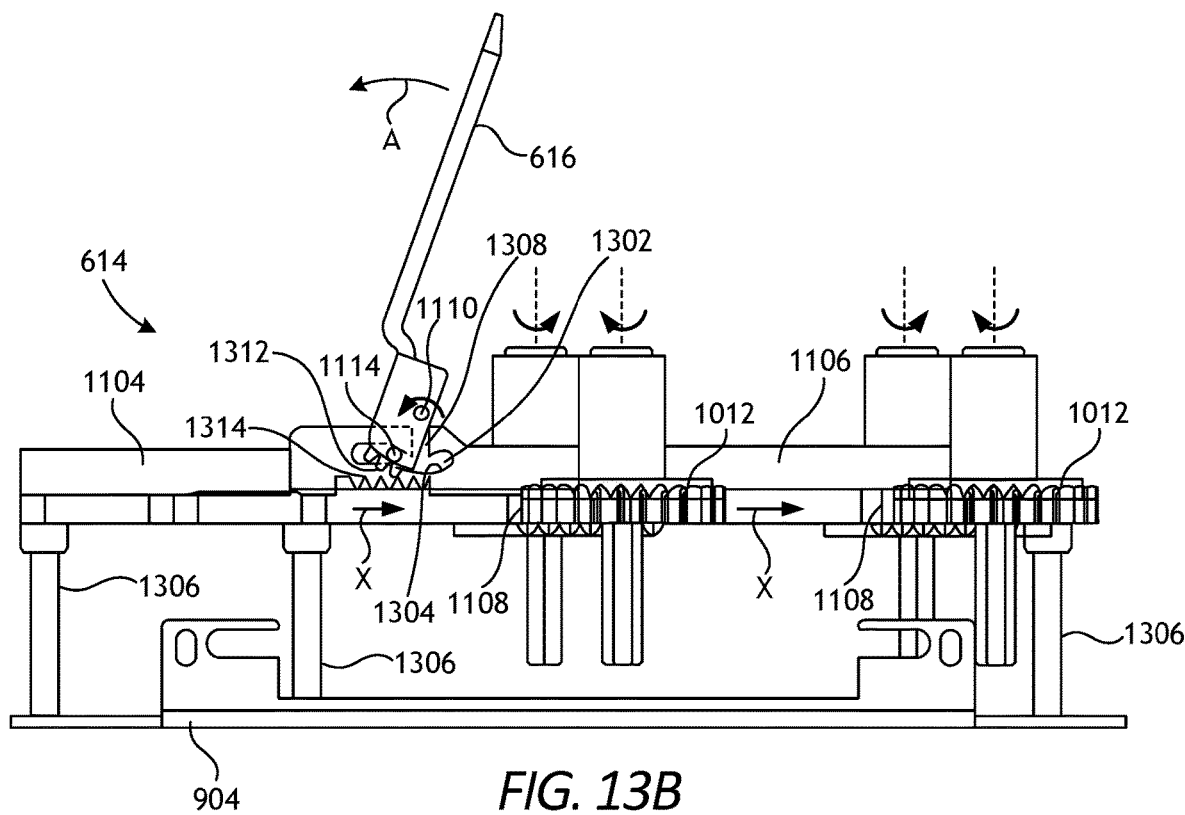
Figure 13C:
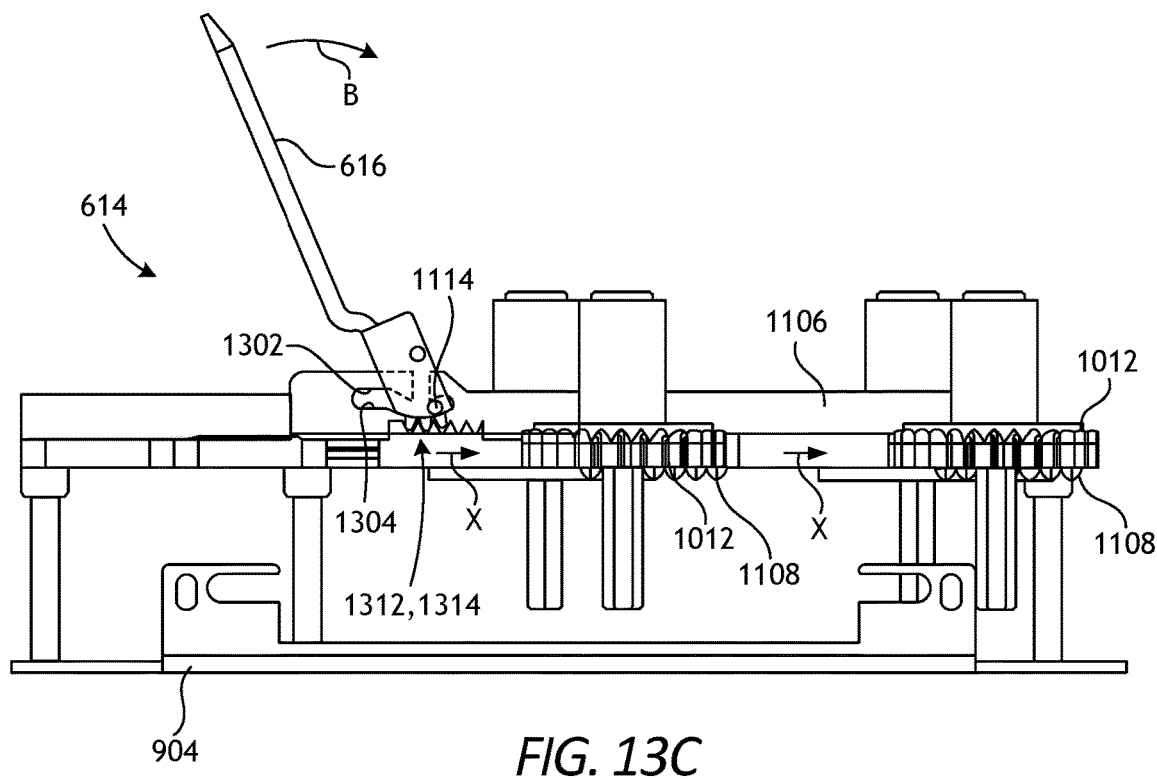

FIGS. 13A-13C are progressive side views of the manual release assembly 614 during example operation, according to one or more embodiments of the disclosure. The release lever 616 is actuatable between a stowed position, as shown in FIG. 13A, and an actuated position, as shown in FIG. 13C. FIG. 13B shows the release lever 616 in an intermediate position between the stowed and actuated positions.

Referring first to FIG. 13A, the manual release assembly 614 may be actuated by grasping the release lever 616 and rotating (pivoting) the release lever 616 about the first pin 1110 (see also FIG. 11) that rotatably couples the release lever 616 to the upper chassis 1102 (FIGS. 11 and 12A-12B) at the support 1112 (FIG. 11). The release lever 616 is shown being rotated (pivoted) in a first angular direction, as shown by the arrow A. As illustrated, the first pin 1110 is received within a drive slot 1302 defined in the jaw release frame 1104 and, more particularly, in the gear rack 1106. The second pin 1114 that movably couples the release lever 616 to the jaw release frame 1104 may also be received within the drive slot 1302.

As the release lever 616 rotates (pivots) about the first pin 1110 in the angular direction A, the second pin 1114 is driven against an inner profile 1304 of the drive slot 1302, which forces the jaw release frame 1104 to move toward the lower chassis 904, as indicated by the arrows. One or more leg pins 1306 (three shown) extend from the jaw release frame 1104, and the jaw release frame 1104 moves toward the lower chassis 904 until the leg pin(s) 1306 engage(s) the upper surface of the lower chassis 904.

FIG. 13B shows the release lever 616 having been rotated further in the angular direction A to the intermediate position. As the jaw release frame 1104 moves toward the lower chassis 904, the first pin 1110 escapes from the drive slot 1302 via an aperture 1308 defined in the drive slot 1302. As the release lever 616 moves toward the intermediate position, the leg pins 1306 are progressively driven against the upper surface of the lower chassis 904, which progressively separates the upper chassis 1102 (FIGS. 11 and 12A-12B) from the lower chassis 904 since the upper chassis 1102 is coupled to the jaw release frame 1104 at the first pin 1110. Moving the upper chassis 1102 away from the lower chassis 904 will disengage the drive inputs 906*c-f* (FIG. 9 and FIGS. 12A-12B) from the drive cable capstans 1010*a-d* (FIGS. 10 and 12A-12B), and thereby freeing the drive cable capstans 1010*a-d* for independent rotation.

The spur gears 1012 are also brought into meshing engagement with the rack gears 1108 provided on the gear rack 1106 as the jaw release frame 1104 moves toward the lower chassis 904. In at least one embodiment, the spur gears 1012 intermesh with the rack gears 1108 prior to the drive inputs 906*c-f* (FIG. 9 and FIGS. 12A-12B) becoming disengaged from the drive cable capstans 1010*a-d* (FIGS. 10 and 12A-12B). This may prove advantageous in locking the rotation of the drive cable capstans 1010*a-d* via the geared interface so the drive cable capstans 1010*a-d* are unable to suddenly release any built up tension.

Continued actuation of the release lever 616 in the angular direction A will move the gear rack 1106 longitudinally in a direction X (e.g., a proximal direction). More specifically, as the release lever 616 continues to rotate (pivot) about the first pin 1110, the second pin 1114 may slidingly engage the inner profile 1304 of the drive slot 1302. The inner profile 1304 may exhibit a geometry that allows teeth 1312 defined on release lever 616 to come into meshing engagement with opposing teeth 1314 defined on the gear rack 1106. Once the opposing teeth 1312, 1314 intermesh, continued movement of the release lever 616 in the angular direction A will urge the gear rack 1106 in the longitudinal direction X and thereby cause the spur gears 1012 to rotate as indicated by the arrows.

FIG. 13C depicts the release lever 616 rotated (pivoted) to the actuated position. In the actuated position, the second pin 1114 has traversed the inner profile 1304 of the drive slot 1302 and the gear rack 1106 has been moved in the longitudinal direction X by virtue of the engagement between the opposing intermeshed teeth 1312, 1314. As the gear rack 1106 translates in the longitudinal direction X, the spur gears 1012 are rotated as engaged with the corresponding rack gears 1108, and rotating the spur gears 1012 correspondingly rotates the drive cable capstans 1010*a-d* (FIGS. 10 and 12A-12B) to manually articulate (e.g., open) the end effector 604 (FIGS. 6 and 8).

As will be appreciated, the manual release assembly 614 is reversible. To transition the release lever 616 back to the stowed position, the user (e.g., a surgeon or clinician) may manually rotate (pivot) the release lever 616 in a second angular direction B, opposite the first angular direction A (FIGS. 13A-13B). This will reverse the foregoing steps and re-engage the drive cable capstans 1010*a-d* (FIGS. 10 and 12A-12B) with the corresponding drive inputs 906*c-f* (FIG. 9 and FIGS. 12A-12B) for normal operation.

Accordingly, the manual release assembly 614 may provide a manual over-ride intervention mechanism that can be included in the surgical tool 600 (FIG. 6) to allow for a "bail-out" function that releases grasped tissue. This may prove advantageous in the event of an electrical disruption that renders the surgical tool 600 inoperable and thus allows the user to release any grasped tissue and remove the surgical tool 600. This may also prove advantageous in cleaning and/or sterilizing the surgical tool 600 where a user is able to manually open the jaws 610, 612 (FIGS. 6 and 8).

Embodiments disclosed herein include:

A. A surgical tool that includes a drive housing that houses a plurality of drive cable capstans operatively coupled to a corresponding plurality of drive inputs, an elongate shaft that extends from the drive housing, an end effector operatively coupled to a distal end of the elongate shaft, a plurality of drive cables extending between the drive housing and the end effector, wherein each drive cable is associated with a corresponding one of the plurality of drive cable capstans and rotation of the plurality of drive cable capstans correspondingly moves the plurality of drive cables to articulate the end effector, and a manual release assembly coupled to the drive housing and including a release lever that is manually movable between a stowed position, where the plurality of drive cable capstans are operatively coupled to the corresponding plurality of drive inputs, and an actuated position, where the plurality of drive cable capstans are disengaged from the corresponding plurality of drive inputs, wherein moving the release lever to the actuated position rotates the plurality of drive cable capstans to manually articulate the end effector.

B. A method of operating a surgical tool that includes positioning the surgical tool adjacent a patient for operation, the surgical tool including a drive housing that houses a plurality of drive cable capstans operatively coupled to a corresponding plurality of drive inputs, an elongate shaft that extends from the drive housing, an end effector operatively coupled to a distal end of the elongate shaft, a plurality of drive cables extending between the drive housing and the end effector, wherein each drive cable is associated with a corresponding one of the plurality of drive cable capstans and rotation of the plurality of drive cable capstans correspondingly moves the plurality of drive cables to articulate the end effector, and a manual release assembly coupled to the drive housing and including a release lever. The method further including manually moving the release lever from a stowed position, where the plurality of drive cable capstans are operatively coupled to the corresponding plurality of drive inputs, to an actuated position, where the plurality of drive cable capstans are disengaged from the corresponding plurality of drive inputs, and rotating the plurality of drive cable capstans to manually articulate the end effector as the release lever is moved to the actuated position.

C. A method of cleaning a surgical tool, the surgical tool including a drive housing that houses a plurality of drive cable capstans operatively coupled to a corresponding plurality of drive inputs, an elongate shaft that extends from the drive housing, an end effector having opposing first and second jaws and being operatively coupled to a distal end of the elongate shaft, a plurality of drive cables extending between the drive housing and the end effector, wherein each drive cable is associated with a corresponding one of the plurality of drive cable capstans, and a manual release assembly coupled to the drive housing and including a release lever that is manually movable between a stowed position and an actuated position, the method comprising manually moving the release lever from a stowed position, where the plurality of drive cable capstans are operatively coupled to the corresponding plurality of drive inputs, to an actuated position, where the plurality of drive cable capstans are disengaged from the corresponding plurality of drive inputs, rotating the plurality of drive cable capstans as the release lever is moved to the actuated position and thereby manually moving the first and second jaws to an open position, and cleaning the first and second jaws.

Each of embodiments A, B, and C may have one or more of the following additional elements in any combination: Element 1: wherein the end effector includes opposing first and second jaws, and wherein moving the release lever to the actuated position moves at least one of the first and second jaws relative to the other and to an open position. Element 2: wherein the release lever is manually movable back to the stowed position to move the at least one of the first and second jaws back to a closed position. Element 3: wherein a chassis is positioned within the drive housing and the release lever is rotatably mounted to the chassis at a first pin, the manual release assembly further comprising a plurality of spur gears, each spur gear being coupled to a corresponding one of the plurality of drive cable capstans for rotation therewith, a jaw release frame including a gear rack that provides one or more rack gears engageable with the plurality of spur gears, and a second pin that movably couples the release lever to the jaw release frame. Element 4: wherein the release lever is rotatable about the first pin to move between the stowed position and the actuated position, and wherein as the release lever moves toward the actuated position, the second pin slidingly engages a drive slot defined in the jaw release frame and moves the one or more rack gears into engagement with the plurality of spur gears. Element 5: wherein the release lever provides teeth engageable with opposing teeth provided on the jaw release frame, and wherein as the release lever moves toward the actuated position, the teeth engage the opposing teeth and the jaw release frame thereby moves longitudinally to rotate the plurality of spur gears. Element 6: wherein the chassis is an upper chassis and the drive housing further includes a lower chassis positioned therein, the manual release assembly further comprising one or more leg pins extending from the jaw release frame and engageable with the lower chassis to disengage the plurality of drive cable capstans from the plurality of drive inputs. Element 7: wherein the lower chassis is compliantly coupled to the drive housing with one or more biasing elements that allow the upper chassis to move relative to the lower chassis. Element 8: wherein the end effector is selected from the group consisting of forceps, a tissue grasper, a needle driver, scissors, an electro cautery tool, a stapler, a clip applier, and any combination thereof.

Element 9: further comprising manually moving the release lever back to the stowed position and thereby re-engaging the plurality of drive cable capstans with the corresponding plurality of drive inputs. Element 10: wherein the end effector includes opposing first and second jaws, and wherein rotating the plurality of drive cable capstans to manually articulate the end effector comprises moving the first and second jaws to an open position. Element 11: further comprising moving the release lever back to the stowed position and thereby moving the first and second jaws back to a closed position. Element 12: wherein the manual release assembly further includes a jaw release frame including a gear rack that provides one or more rack gears, and a plurality of spur gears, each spur gear being coupled to a corresponding one of the plurality of drive cable capstans for rotation therewith, and wherein manually moving the release lever from the stowed position to the actuated position comprises rotating the release lever about a first pin that couples the release lever to a chassis positioned within the drive housing, and moving the one or more rack gears into meshed engagement with the plurality of spur gears. Element 13: wherein the release lever is movably coupled to the jaw release frame at a second pin positioned within a drive slot defined by the jaw release frame, and wherein moving the one or more rack gears into meshed engagement with the plurality of spur gears comprises slidingly engaging the second pin within the drive slot, and driving the second pin against an inner profile of the drive slot and thereby forcing the jaw release frame to move the one or more rack gears into meshed engagement with the plurality of spur gears. Element 14: wherein the release lever provides teeth and the jaw release frame provides opposing teeth, and wherein manually moving the release lever from the stowed position to the actuated position comprises engaging the teeth against the opposing teeth, and moving the jaw release frame longitudinally via engagement between the teeth and the opposing teeth and thereby rotating the plurality of spur gears. Element 15: wherein the chassis is an upper chassis and the drive housing further includes a lower chassis positioned therein, and wherein driving the second pin against an inner profile of the drive slot further comprises engaging one or more leg pins extending from the jaw release frame against the lower chassis, and disengaging the plurality of drive cable capstans from the plurality of drive inputs as the one or more leg pins are driven against the lower chassis. Element 16: wherein the lower chassis is compliantly coupled to the drive housing with one or more biasing elements, the method further comprising manually moving the release lever back to the stowed position and thereby allowing spring force of the one or more biasing elements to move the lower chassis back toward the upper chassis, and re-engaging the plurality of drive cable capstans with the corresponding plurality of drive inputs.

By way of non-limiting example, exemplary combinations applicable to A, B, and C include: Element 1 with Element 2; Element 3 with Element 4; Element 4 with Element 5; Element 3 with Element 6; Element 6 with Element 7; Element 10 with Element 11; Element 13 with Element 14; Element 14 with Element 15; and Element 15 with Element 16.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A surgical tool, comprising:
   a drive housing that houses a plurality of drive cable capstans operatively coupled to a corresponding plurality of drive inputs;
   an elongate shaft that extends from the drive housing;
   an end effector operatively coupled to a distal end of the elongate shaft;
   a plurality of drive cables extending between the drive housing and the end effector, wherein each drive cable is associated with a corresponding one of the plurality of drive cable capstans and rotation of the plurality of drive cable capstans correspondingly moves the plurality of drive cables to articulate the end effector; and
   a manual release assembly coupled to the drive housing and including a release lever that is manually movable between a stowed position, where the plurality of drive cable capstans are operatively coupled to the corresponding plurality of drive inputs, and an actuated position, where the plurality of drive cable capstans are disengaged from the corresponding plurality of drive inputs,
   wherein moving the release lever to the actuated position rotates the plurality of drive cable capstans to manually articulate the end effector.

2. The surgical tool of claim 1, wherein the end effector includes opposing first and second jaws, and wherein moving the release lever to the actuated position moves at least one of the first and second jaws relative to the other and to an open position.

3. The surgical tool of claim 2, wherein the release lever is manually movable back to the stowed position to move the at least one of the first and second jaws back to a closed position.

4. The surgical tool of claim 1, wherein a chassis is positioned within the drive housing and the release lever is rotatably mounted to the chassis at a first pin, the manual release assembly further comprising:
   a plurality of spur gears, each spur gear being coupled to a corresponding one of the plurality of drive cable capstans for rotation therewith;
   a jaw release frame including a gear rack that provides one or more rack gears engageable with the plurality of spur gears; and
   a second pin that movably couples the release lever to the jaw release frame.

5. The surgical tool of claim 4, wherein the release lever is rotatable about the first pin to move between the stowed position and the actuated position, and wherein as the release lever moves toward the actuated position, the second pin slidingly engages a drive slot defined in the jaw release frame and moves the one or more rack gears into engagement with the plurality of spur gears.

6. The surgical tool of claim 5, wherein the release lever provides teeth engageable with opposing teeth provided on the jaw release frame, and wherein as the release lever moves toward the actuated position, the teeth engage the opposing teeth and the jaw release frame thereby moves longitudinally to rotate the plurality of spur gears.

7. The surgical tool of claim 4, wherein the chassis is an upper chassis and the drive housing further includes a lower chassis positioned therein, the manual release assembly further comprising:
   one or more leg pins extending from the jaw release frame and engageable with the lower chassis to disengage the plurality of drive cable capstans from the plurality of drive inputs.

8. The surgical tool of claim 7, wherein the lower chassis is compliantly coupled to the drive housing with one or more biasing elements that allow the upper chassis to move relative to the lower chassis.

9. The surgical tool of claim 1, wherein the end effector is selected from the group consisting of forceps, a tissue grasper, a needle driver, scissors, an electro cautery tool, a stapler, a clip applier, and any combination thereof.

10. A method of operating a surgical tool, comprising:
    positioning the surgical tool adjacent a patient for operation, the surgical tool including:

a drive housing that houses a plurality of drive cable capstans operatively coupled to a corresponding plurality of drive inputs;

an elongate shaft that extends from the drive housing;

an end effector operatively coupled to a distal end of the elongate shaft;

a plurality of drive cables extending between the drive housing and the end effector, wherein each drive cable is associated with a corresponding one of the plurality of drive cable capstans and rotation of the plurality of drive cable capstans correspondingly moves the plurality of drive cables to articulate the end effector; and a manual release assembly coupled to the drive housing and including a release lever;

manually moving the release lever from a stowed position, where the plurality of drive cable capstans are operatively coupled to the corresponding plurality of drive inputs, to an actuated position, where the plurality of drive cable capstans are disengaged from the corresponding plurality of drive inputs; and rotating the plurality of drive cable capstans to manually articulate the end effector as the release lever is moved to the actuated position.

11. The method of claim 10, further comprising manually moving the release lever back to the stowed position and thereby re-engaging the plurality of drive cable capstans with the corresponding plurality of drive inputs.

12. The method of claim 10, wherein the end effector includes opposing first and second jaws, and wherein rotating the plurality of drive cable capstans to manually articulate the end effector comprises moving the first and second jaws to an open position.

13. The method of claim 12, further comprising moving the release lever back to the stowed position and thereby moving the first and second jaws back to a closed position.

14. The method of claim 10, wherein the manual release assembly further includes a jaw release frame including a gear rack that provides one or more rack gears, and a plurality of spur gears, each spur gear being coupled to a corresponding one of the plurality of drive cable capstans for rotation therewith, and wherein manually moving the release lever from the stowed position to the actuated position comprises:

rotating the release lever about a first pin that couples the release lever to a chassis positioned within the drive housing; and moving the one or more rack gears into meshed engagement with the plurality of spur gears.

15. The method of claim 14, wherein the release lever is movably coupled to the jaw release frame at a second pin positioned within a drive slot defined by the jaw release frame, and wherein moving the one or more rack gears into meshed engagement with the plurality of spur gears comprises:

slidingly engaging the second pin within the drive slot; and driving the second pin against an inner profile of the drive slot and thereby forcing the jaw release frame to move the one or more rack gears into meshed engagement with the plurality of spur gears.

16. The method of claim 15, wherein the release lever provides teeth and the jaw release frame provides opposing teeth, and wherein manually moving the release lever from the stowed position to the actuated position comprises:

engaging the teeth against the opposing teeth; and moving the jaw release frame longitudinally via engagement between the teeth and the opposing teeth and thereby rotating the plurality of spur gears.

17. The method of claim 15, wherein the chassis is an upper chassis and the drive housing further includes a lower chassis positioned therein, and wherein driving the second pin against an inner profile of the drive slot further comprises:

engaging one or more leg pins extending from the jaw release frame against the lower chassis; and disengaging the plurality of drive cable capstans from the plurality of drive inputs as the one or more leg pins are driven against the lower chassis.

18. The method of claim 17, wherein the lower chassis is compliantly coupled to the drive housing with one or more biasing elements, the method further comprising:

manually moving the release lever back to the stowed position and thereby allowing spring force of the one or more biasing elements to move the lower chassis back toward the upper chassis; and re-engaging the plurality of drive cable capstans with the corresponding plurality of drive inputs.

19. A method of cleaning a surgical tool, the surgical tool including a drive housing that houses a plurality of drive cable capstans operatively coupled to a corresponding plurality of drive inputs, an elongate shaft that extends from the drive housing, an end effector having opposing first and second jaws and being operatively coupled to a distal end of the elongate shaft, a plurality of drive cables extending between the drive housing and the end effector, wherein each drive cable is associated with a corresponding one of the plurality of drive cable capstans, and a manual release assembly coupled to the drive housing and including a release lever that is manually movable between a stowed position and an actuated position, the method comprising:

manually moving the release lever from a stowed position, where the plurality of drive cable capstans are operatively coupled to the corresponding plurality of drive inputs, to an actuated position, where the plurality of drive cable capstans are disengaged from the corresponding plurality of drive inputs;

rotating the plurality of drive cable capstans as the release lever is moved to the actuated position and thereby manually moving the first and second jaws to an open position; and cleaning the first and second jaws.

* * * * *